(12) United States Patent
Krishnaswamy et al.

(10) Patent No.: US 8,750,857 B2
(45) Date of Patent: Jun. 10, 2014

(54) METHOD AND APPARATUS FOR WIRELESS DISTRIBUTED COMPUTING

(75) Inventors: Dilip Krishnaswamy, San Diego, CA (US); Subbarao V. Yallapragada, San Diego, CA (US); Sanjiv Nanda, Ramona, CA (US); Soumya Das, San Diego, CA (US); Samir Salib Soliman, San Diego, CA (US); Peerapol Tinnakornsrisuphap, San Diego, CA (US); Vidya Narayanan, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 325 days.

(21) Appl. No.: 12/959,206

(22) Filed: Dec. 2, 2010

(65) Prior Publication Data

US 2011/0300851 A1 Dec. 8, 2011

Related U.S. Application Data

(60) Provisional application No. 61/351,725, filed on Jun. 4, 2010.

(51) Int. Cl.
| | |
|---|---|
| *H04W 4/00* | (2009.01) |
| *H04W 72/00* | (2009.01) |
| *H04W 88/02* | (2009.01) |
| *H04W 4/02* | (2009.01) |
| *H04W 88/06* | (2009.01) |

(52) U.S. Cl.
CPC ............... *H04W 88/02* (2013.01); *H04W 4/02* (2013.01); *H04W 88/06* (2013.01)
USPC ........ 455/422.1; 455/453; 370/329; 370/331; 370/350; 370/445; 375/130; 375/222; 709/201; 709/219; 712/12

(58) Field of Classification Search
USPC ............... 455/422.1, 453; 370/329, 331, 350, 370/445; 375/130, 222; 712/12; 701/24; 709/201, 219
See application file for complete search history.

(56) References Cited

U.S. PATENT DOCUMENTS 4,933,836 A * 6/1990 Tulpule et al. .................. 712/12
4,975,907 A * 12/1990 Dutruel et al. ................ 370/445

(Continued)

FOREIGN PATENT DOCUMENTS

| EP | 2043404 A1 | 4/2009 |
| EP | 2131614 A1 | 12/2009 |

(Continued)

OTHER PUBLICATIONS

International Search Report and Written Opinion—PCT/US2011/039176—ISA/EPO—Oct. 4, 2011.

(Continued)

*Primary Examiner* — William D Cumming

(57) ABSTRACT

Systems and methods for distributed computing between communication devices. A femto node is treated as a trusted extension of a user equipment and performs processing tasks on behalf of the user equipment. The femto node is also treated as a trusted extension of network servers and performs services on behalf of the network servers. Tasks are thus distributed between the network servers, the femto node and one or more user equipments. The tasks include processing data, filtering incoming messages, and caching network service information.

48 Claims, 14 Drawing Sheets

(56) References Cited

U.S. PATENT DOCUMENTS

| | | | |
|---|---|---|---|
| 6,690,719 B1* | 2/2004 | Raphaeli et al. | 375/222 |
| 7,606,290 B1* | 10/2009 | Chavez et al. | 375/130 |
| 8,139,526 B2* | 3/2012 | Zhou et al. | 370/329 |
| 8,254,368 B2* | 8/2012 | Huber et al. | 370/350 |
| 8,406,733 B2 | 3/2013 | Raleigh | |
| 2007/0174290 A1 | 7/2007 | Narang et al. | |
| 2008/0090585 A1* | 4/2008 | Hart et al. | 455/453 |
| 2009/0094683 A1 | 4/2009 | Morgan et al. | |
| 2009/0300689 A1 | 12/2009 | Conte et al. | |
| 2010/0070417 A1 | 3/2010 | Flynn et al. | |
| 2010/0082193 A1* | 4/2010 | Chiappetta | 701/24 |
| 2011/0300851 A1* | 12/2011 | Krishnaswamy et al. | 455/422.1 |
| 2011/0300852 A1* | 12/2011 | Krishnaswamy et al. | 455/422.1 |
| 2012/0170548 A1* | 7/2012 | Rajagopalan et al. | 370/331 |
| 2012/0185569 A1* | 7/2012 | Das et al. | 709/219 |
| 2012/0246212 A1* | 9/2012 | Ahmad et al. | 709/201 |
| 2013/0063302 A1 | 3/2013 | Krasner et al. | |
| 2013/0063307 A1 | 3/2013 | Krasner et al. | |
| 2013/0063308 A1 | 3/2013 | Krasner et al. | |
| 2013/0066717 A1 | 3/2013 | Marovets | |
| 2013/0072149 A1 | 3/2013 | Raleigh | |
| 2013/0080607 A1 | 3/2013 | Raleigh | |

FOREIGN PATENT DOCUMENTS

| | | |
|---|---|---|
| JP | 2002330230 A | 11/2002 |
| JP | 2008092129 A | 4/2008 |
| JP | 2008175824 A | 7/2008 |
| WO | WO2011010601 A1 | 1/2011 |

OTHER PUBLICATIONS

NEC: "Discussion on requirements for digital content sharing with LIPA", 3GPP Draft, S1-094015, 3rd Generation Partnership Project (3GPP), Mobile Competence Centre, 650, Route Des Lucioles, F-06921 Sophia-Antipolis Cedex, France, No. Beijing, 20091116, Nov. 16, 2009, XP050395999, [retrieved on Nov. 9, 2009].

Verizon: "DLNA parameter categories and justification for HeNB", 3GPP Draft; S5EHNB0009, No. Shanghai, China; 20091113, Sep. 28, 2009, XP050399130, [retrieved on Sep. 28, 2009].

* cited by examiner

US 8,750,857 B2

METHOD AND APPARATUS FOR WIRELESS DISTRIBUTED COMPUTING

CROSS REFERENCE TO RELATED APPLICATION(S)

This application claims the benefit of U.S. Provisional Application No. 61/351,725, filed Jun. 4, 2010, the entire content of which is incorporated herein by reference.

The present Application for Patent is related to co-pending U.S. patent application Ser. No. 12/959,223, entitled "METHOD AND APPARATUS FOR WIRELESS DISTRIBUTED COMPUTING," filed concurrently herewith, assigned to the assignee hereof, and expressly incorporated by reference herein.

BACKGROUND

1. Field

The present application relates generally to wireless communication, and more specifically to systems and methods for distributing computing between communication devices.

2. Background

Wireless communication systems are widely deployed to provide various types of communication (e.g., voice, data, multimedia services, etc.) to multiple users. As the demand for high-rate and multimedia data services rapidly grows, there lies a challenge to implement efficient and robust communication systems with enhanced performance.

In addition to mobile phone networks currently in place, a new class of small base stations has emerged, which may be installed in a user's home and provide indoor wireless coverage to mobile units using existing broadband Internet connections. Such personal miniature base stations are generally known as access point base stations, or, alternatively, Home Node B (HNB), femto access points, or femto nodes. Typically, such miniature base stations are connected to the Internet and the mobile operator's network via a DSL router or a cable modem. Multiple femto nodes may be deployed by individual users in the coverage area of a traditional macro node. Femto nodes may form part of local networks and may be connected to various devices. A user's mobile unit may be constrained in terms of power, bandwidth, or processing capability. Thus it may be desirable to reallocate certain processing tasks from the user's mobile unit to a less constrained device.

SUMMARY

The systems, methods, and devices of the invention each have several aspects, no single one of which is solely responsible for its desirable attributes. Without limiting the scope of this invention as expressed by the claims which follow, some features will now be discussed briefly. After considering this discussion, and particularly after reading the section entitled "Detailed Description" one will understand how the features of this invention provide advantages that include distributed computing between communication devices In one aspect a method of communication is provided. The method includes receiving, by a femto node, a first communication from a first apparatus, the first communication comprising an indication of one or more processing tasks to perform, performing the one or more processing tasks, and selectively transmitting a second communication to a second apparatus, the second communication comprising an indication of a result of the one or more processing tasks.

In another aspect, a femto node is provided. The femto node includes a receiver configured to receive a first communication from a first apparatus, the first communication comprising an indication of one or more processing tasks to perform, a processor configured to perform the one or more processing tasks, and a transmitter configured to selectively transmit a second communication to a second apparatus, the second communication comprising an indication of a result of the one or more processing tasks.

In another aspect a femto node is provided. The femto node includes means for receiving a first communication from a first apparatus, the first communication comprising an indication of one or more processing tasks to perform, means for performing the one or more processing tasks, and means for transmitting a second communication to a second apparatus, the second communication comprising an indication of a result of the one or more processing tasks.

In another aspect, a computer program product is provided. The product includes a computer-readable medium. The medium includes code for causing a computer to receive, by a femto node, a first communication from a first apparatus, the first communication comprising an indication of one or more processing tasks to perform, code for causing a computer to perform the one or more processing tasks, and code for causing a computer to selectively transmit a second communication to a second apparatus, the second communication comprising an indication of a result of the one or more processing tasks.

In another aspect, a method of communication is provided. The method includes determining, by an apparatus, one or more processing tasks to be offloaded to a femto node, generating a first communication comprising an indication of the one or more processing tasks, transmitting the first communication to the femto node, and receiving a second communication from the femto node comprising an indication of a result of the one or more processing tasks.

In another aspect, an apparatus for communication is provided. The apparatus includes a processor configured to determine one or more processing tasks to be offloaded to a femto node and generate a first communication comprising an indication of the one or more processing tasks, a transmitter configured to transmit the first communication to the femto node, and a receiving configured to receive a second communication from the femto node comprising an indication of a result of the one or more processing tasks.

In another aspect, an apparatus for communication is provided. The apparatus includes means for determining one or more processing tasks to be offloaded to a femto node, means for generating a first communication comprising an indication of the one or more processing tasks, means for transmitting the first communication to the femto node, and means for receiving a second communication from the femto node comprising an indication of a result of the one or more processing tasks.

In another aspect, a computer program product is provided. The product includes a computer-readable medium. The medium includes code for causing a computer to determine, by an apparatus, one or more processing tasks to be offloaded to a femto node, code for causing a computer to generate a first communication comprising an indication of the one or more processing tasks, code for causing a computer to transmit the first communication to the femto node, and code for causing a computer to receive a second communication from the femto node comprising an indication of a result of the one or more processing tasks.

In another aspect, a method of communication is provided. The method includes receiving, by a femto node, a communication from a server, determining one or more processing tasks to be performed on information in the communication, performing the one or more processing task on the information in the communication, and transmitting the result of the one or more processing tasks to a user equipment.

In another aspect, a femto node is provided. The femto node includes a receiver configured to receive a communication from a server, a processor configured to determine one or more processing tasks to be performed on information in the communication and perform the one or more processing task on the information in the communication, and a transmitter configured to transmit the result of the one or more processing tasks to a user equipment.

In another aspect, a femto node is provided. The femto node includes means for receiving a communication from a server, means for determining one or more processing tasks to be performed on information in the communication, means for performing the one or more processing task on the information in the communication, and means for transmitting the result of the one or more processing tasks to a user equipment.

In another aspect, a computer program product is provided. The product includes a computer-readable medium. The medium includes code for causing a computer to receive, by a femto node, a communication from a server, code for causing a computer to determine one or more processing tasks to be performed on information in the communication, code for causing a computer to perform the one or more processing task on the information in the communication, and code for causing a computer to transmit the result of the one or more processing tasks to a user equipment.

DETAILED DESCRIPTION

Figure 1:
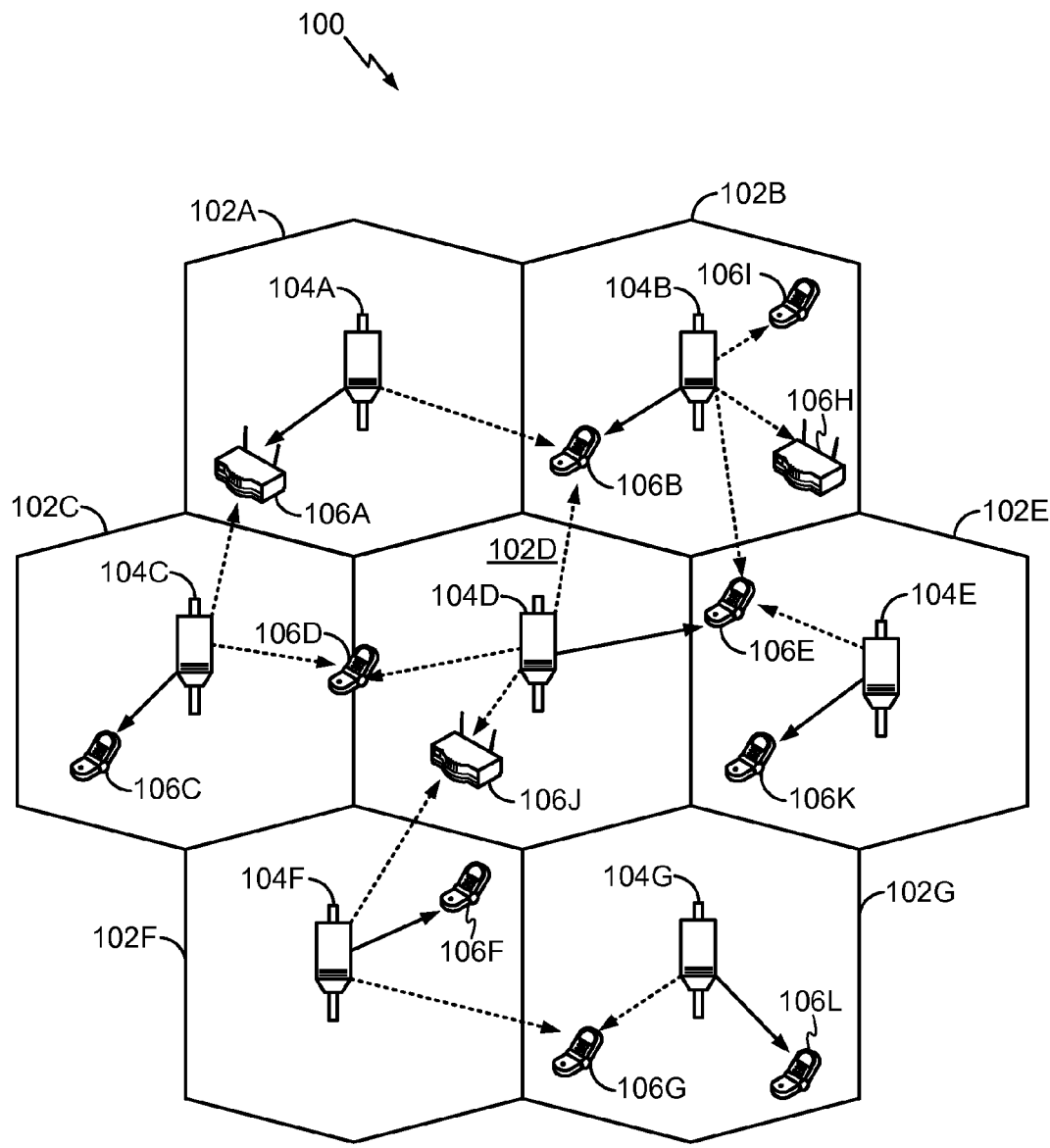
FIG. 1 illustrates an exemplary wireless communication network.

The word "exemplary" is used herein to mean "serving as an example, instance, or illustration." Any embodiment described herein as "exemplary" is not necessarily to be construed as preferred or advantageous over other embodiments. The techniques described herein may be used for various wireless communication networks such as Code Division Multiple Access (CDMA) networks, Time Division Multiple Access (TDMA) networks, Frequency Division Multiple Access (FDMA) networks, Orthogonal FDMA (OFDMA) networks, Single-Carrier FDMA (SC-FDMA) networks, etc. The terms "networks" and "systems" are often used interchangeably. A CDMA network may implement a radio technology such as Universal Terrestrial Radio Access (UTRA), cdma2000, etc. UTRA includes Wideband-CDMA (W-CDMA) and Low Chip Rate (LCR). cdma2000 covers IS-2000, IS-95 and IS-856 standards. A TDMA network may implement a radio technology such as Global System for Mobile Communications (GSM). An OFDMA network may implement a radio technology such as Evolved UTRA (E-UTRA), IEEE 802.11, IEEE 802.16, IEEE 802.20, Flash-OFDMA, etc. UTRA, E-UTRA, and GSM are part of Universal Mobile Telecommunication System (UMTS). Long Term Evolution (LTE) is an upcoming release of UMTS that uses E-UTRA. UTRA, E-UTRA, GSM, UMTS and LTE are described in documents from an organization named "3rd Generation Partnership Project" (3GPP). cdma2000 is described in documents from an organization named "3rd Generation Partnership Project 2" (3GPP2). These various radio technologies and standards are known in the art.

Single carrier frequency division multiple access (SC-FDMA), which utilizes single carrier modulation and frequency domain equalization is a technique. SC-FDMA has similar performance and essentially the same overall complexity as those of OFDMA system. SC-FDMA signal has lower peak-to-average power ratio (PAPR) because of its inherent single carrier structure. SC-FDMA has drawn great attention, especially in the uplink communications where lower PAPR greatly benefits the mobile terminal in terms of transmit power efficiency. It is currently a working assumption for uplink multiple access scheme in 3GPP Long Term Evolution (LTE), or Evolved UTRA.

In some aspects the teachings herein may be employed in a network that includes macro scale coverage (e.g., a large area cellular network such as a 3G networks, typically referred to as a macro cell network) and smaller scale coverage (e.g., a residence-based or building-based network environment). As a user equipment ("UE") moves through such a network, the user equipment may be served in certain locations by access nodes ("ANs") that provide macro coverage while the user equipment may be served at other locations by access nodes that provide smaller scale coverage. In some aspects, the smaller coverage nodes may be used to provide incremental capacity growth, in-building coverage, and different services (e.g., for a more robust user experience). In the discussion herein, a node that provides coverage over a relatively large area may be referred to as a macro node. A node that provides coverage over a relatively small area (e.g., a residence) may be referred to as a femto node. A node that provides coverage over an area that is smaller than a macro area and larger than a femto area may be referred to as a pico node (e.g., providing coverage within a commercial building).

A cell associated with a macro node, a femto node, or a pico node may be referred to as a macro cell, a femto cell, or a pico cell, respectively. In some implementations, each cell may be further associated with (e.g., divided into) one or more sectors.

In various applications, other terminology may be used to reference a macro node, a femto node, or a pico node. For example, a macro node may be configured or referred to as an access node, base station, access point, eNodeB, macro cell, and so on. Also, a femto node may be configured or referred to as a Home NodeB, Home eNodeB, access point base station, femto cell, and so on.

FIG. 1 illustrates an exemplary wireless communication network 100. The wireless communication network 100 is configured to support communication between a number of users. The wireless communication network 100 may be divided into one or more cells 102, such as, for example, cells 102a-102g. Communication coverage in cells 102a-102g may be provided by one or more nodes 104, such as, for example, nodes 104a-104g. Each node 104 may provide communication coverage to a corresponding cell 102. The nodes 104 may interact with a plurality of user equipments (UEs), such as, for example, UEs 106a-106l.

Each UE 106 may communicate with one or more nodes 104 on a forward link (FL) and/or a reverse link (RL) at a given moment. A FL is a communication link from a node to a UE. A RL is a communication link from a UE to a node. The nodes 104 may be interconnected, for example, by appropriate wired or wireless interfaces and may be able to communicate with each other. Accordingly, each UE 106 may communicate with another UE 106 through one or more nodes 104. For example, the UE 106j may communicate with the UE 106h as follows. The UE 106j may communicate with the node 104d. The node 104d may then communicate with the node 104b. The node 104b may then communicate with the UE 106h. Accordingly, a communication is established between the UE 106j and the UE 106h.

The wireless communication network 100 may provide service over a large geographic region. For example, the cells 102a-102g may cover only a few blocks within a neighborhood or several square miles in a rural environment. In one embodiment, each cell may be further divided into one or more sectors (not shown).

As described above, a node 104 may provide a user equipment (UE) 106 access within its coverage area to a communications network, such as, for example the internet or a cellular network.

A UE 106 may be a wireless communication device (e.g., a mobile phone, router, personal computer, server, etc.) used by a user to send and receive voice or data over a communications network. A user equipment (UE) may also be referred to herein as an access terminal (AT), as a mobile station (MS), or as a terminal device. As shown, UEs 106a, 106h, and 106j comprise routers. UEs 106b-106g, 106i, 106k, and 106l comprise mobile phones. However, each of UEs 106a-106l may comprise any suitable communication device.

Figure 2:
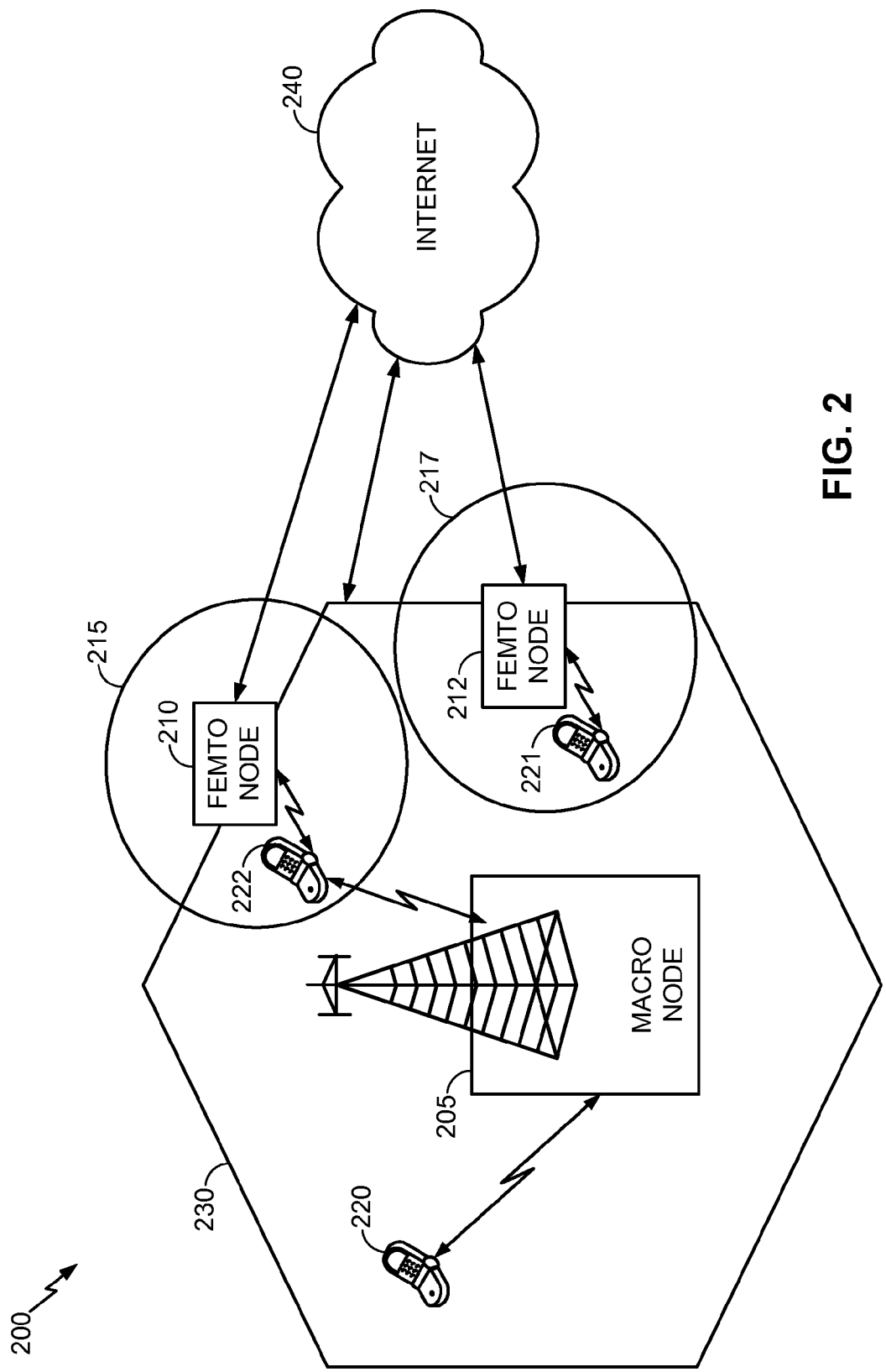
FIG. 2 illustrates exemplary interoperations of two or more communication networks.

FIG. 2 illustrates exemplary interoperations of two or more communication networks. It may desirable for a UE 220 to transmit information to and receive information from another UE such as UE 221. FIG. 2 illustrates a manner in which the UEs 220, 221, and 222 may communicate with each other. As shown in FIG. 2, the macro node 205 may provide communication coverage to user equipments within a macro area 230. For example, the UE 220 may generate and transmit a message to the macro node 205. The message may comprise information related to various types of communication (e.g., voice, data, multimedia services, etc.). The UE 220 may communicate with the macro node 205 via a wireless link. The macro node 205 may communicate with a network 240 via a wired link or via a wireless link. The femto nodes 210 and 212 may also communicate with the network 240 via a wired link or via a wireless link. The UE 222 may communicate with the femto node 210 via a wireless link and the UE 221 may communicate with the femto node 212 via a wireless link.

The macro node 205 may also communicate with devices such as servers (not shown in FIG. 2) and switching centers (not shown in FIG. 2) through the network 240. For example, the macro node 205 may transmit the message received from the UE 220 to a switching center (not shown in FIG. 2), which may forward the message to another network. The network 240 may also be used to facilitate communication between the UEs 220, 221, and 222. For example, the UE 220 may be in communication with the UE 221. The UE 220 may transmit a message to the macro node 205. The macro node 205 may forward the message to the network 240. The network 240 may forward the messages to the femto node 212. The femto node 212 may forward the message to the UE 221. Similarly, the reverse path may be followed from the UE 221 to the UE 220. In another example, the UE 221 may be in communication with the UE 222. The UE 221 may transmit a message to the femto node 212. The femto node 212 may forward the message to the network 240. The network 240 may forward the message to the femto node 210. The femto node 210 may forward the message to the UE 222. Similarly, the reverse path may be followed from the UE 222 to the UE 221.

In one embodiment, the femto nodes 210, 212 may be deployed by individual consumers and placed in homes, apartment buildings, office buildings, and the like. The femto nodes 210, 212 may communicate with the UEs in a predetermined range (e.g., 100 m) of the femto nodes 210, 212 utilizing a predetermined cellular transmission band. In one embodiment, the femto nodes 210, 212 may communicate with the network 240 by way of an Internet Protocol (IP) connection, such as a digital subscriber line (DSL, e.g., including asymmetric DSL (ADSL), high data rate DSL (HDSL), very high speed DSL (VDSL), etc.), a TV cable carrying Internet Protocol (IP) traffic, a broadband over power line (BPL) connection, or other link.

The network 240 may comprise any type of electronically connected group of computers and/or devices including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) Asynchronous Transfer Mode (ATM), Wireless Ethernet (IEEE 802.11), or Bluetooth (IEEE 802.15.1). Note that computing devices may be desktop, server, portable, hand-held, set-top, or any other desired type of configuration. As used herein, the network 240 includes network variations such as the public Internet, a private network within the Internet, a secure network within the Internet, a private network, a public network, a value-added network, an intranet, and the like. In certain embodiments, network 240 may also comprise a virtual private network (VPN).

Figure 3:
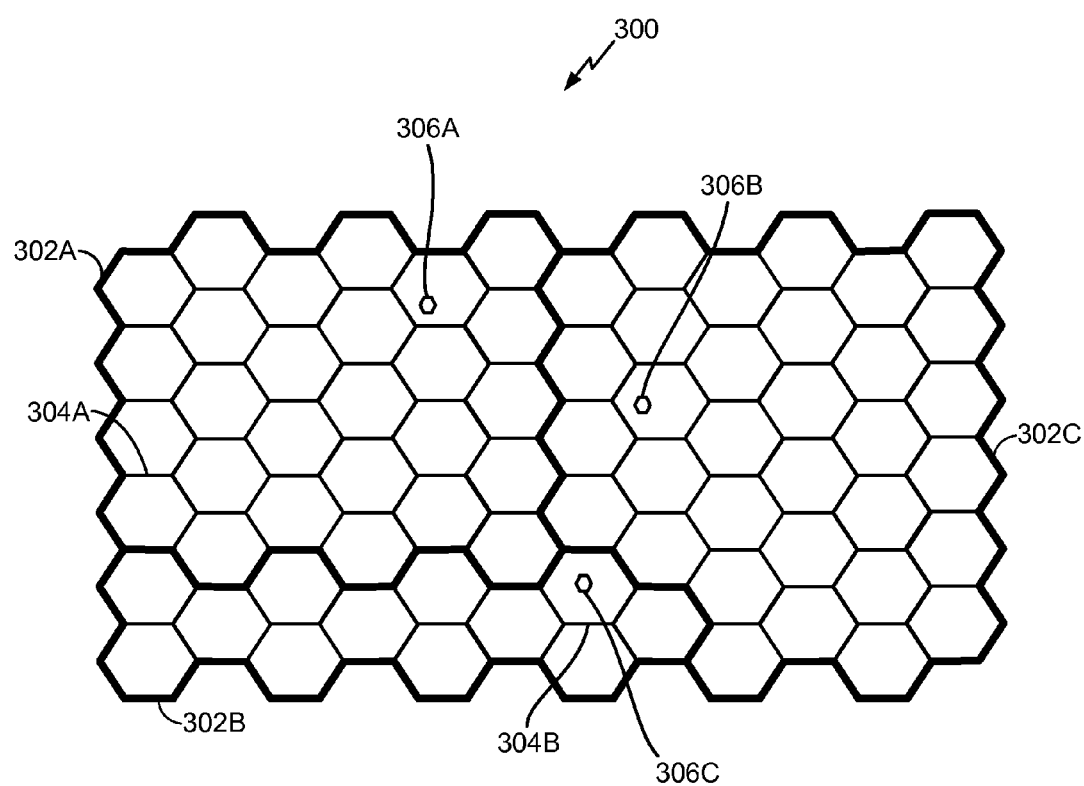
FIG. 3 illustrates exemplary coverage areas of the wireless communication networks shown in FIGS. 1 and 2.

FIG. 3 illustrates exemplary coverage areas of the wireless communication networks 100 and 200 shown in FIGS. 1 and 2. The coverage area 300 may comprise one or more geographical areas in which the UE 220 may access the communication network 240 as discussed above with respect to FIG. 2. As shown the coverage area 300 comprises several tracking areas 302 (or routing areas or location areas). Each tracking area 302 comprises several macro areas 304, which may be similar to the macro area 230 described above with respect to FIG. 2. Here, areas of coverage associated with tracking areas 302A, 302B, and 302C are shown as delineated by wide lines as and the macro areas 304 are represented by hexagons. The tracking areas 302 may also comprise femto areas 306, which may be similar to the femto area 230 described above with respect to FIG. 2. In this example, each of the femto areas 306 (e.g., femto area 306C) is depicted within a macro area 304

(e.g., macro area 304B). It should be appreciated, however, that a femto area 306 may not lie entirely within a macro area 304. In practice, a large number of femto areas 306 may be defined with a given tracking area 302 or macro area 304. Also, one or more pico areas (not shown) may be defined within a given tracking area 302 or macro area 304. As described below, in some embodiments, the femto areas 306 may comprise local networks which facilitate network communication access by one or more local network devices. It may be desirable for a UE 220 to communicate with one or more of the devices in a femto area local network even when the UE 220 is located remotely. Systems and methods for facilitating secure remote access to femto area local networks are described herein.

For convenience, the disclosure herein describes various functionalities related to a femto node. It should be appreciated, however, that a pico node may provide the same or similar functionality for a larger coverage area. For example, a pico node may be restricted, a home pico node may be defined for a given user equipment, and so on.

A wireless multiple-access communication system may simultaneously support communication for multiple wireless user equipments. As mentioned above, each user equipment may communicate with one or more nodes via transmissions on the forward and reverse links. The forward link (or downlink) refers to the communication link from the node to the user equipment, and the reverse link (or uplink) refers to the communication link from the user equipment to the node. This communication link may be established via a single-in-single-out system, a multiple-in-multiple-out ("MIMO") system, or some other type of system.

A MIMO system employs multiple (NT) transmit antennas and multiple (NR) receive antennas for data transmission. A MIMO channel formed by the NT transmit and NR receive antennas may be comprise NS independent channels, which are also referred to as spatial channels, where NS≤min {NT, NR}. Each of the NS independent channels corresponds to a dimension. The MIMO system may provide improved performance (e.g., higher throughput and/or greater reliability) if the additional dimensionalities created by the multiple transmit and receive antennas are utilized.

A MIMO system may support time division duplex ("TDD") and frequency division duplex ("FDD"). In a TDD system, the forward and reverse link transmissions are on the same frequency region so that the reciprocity principle allows the estimation of the forward link channel from the reverse link channel. This enables a device (e.g., a node, a user equipment, etc.) to extract a transmit beam-forming gain on the forward link when multiple antennas are available at the device.

Figure 4:
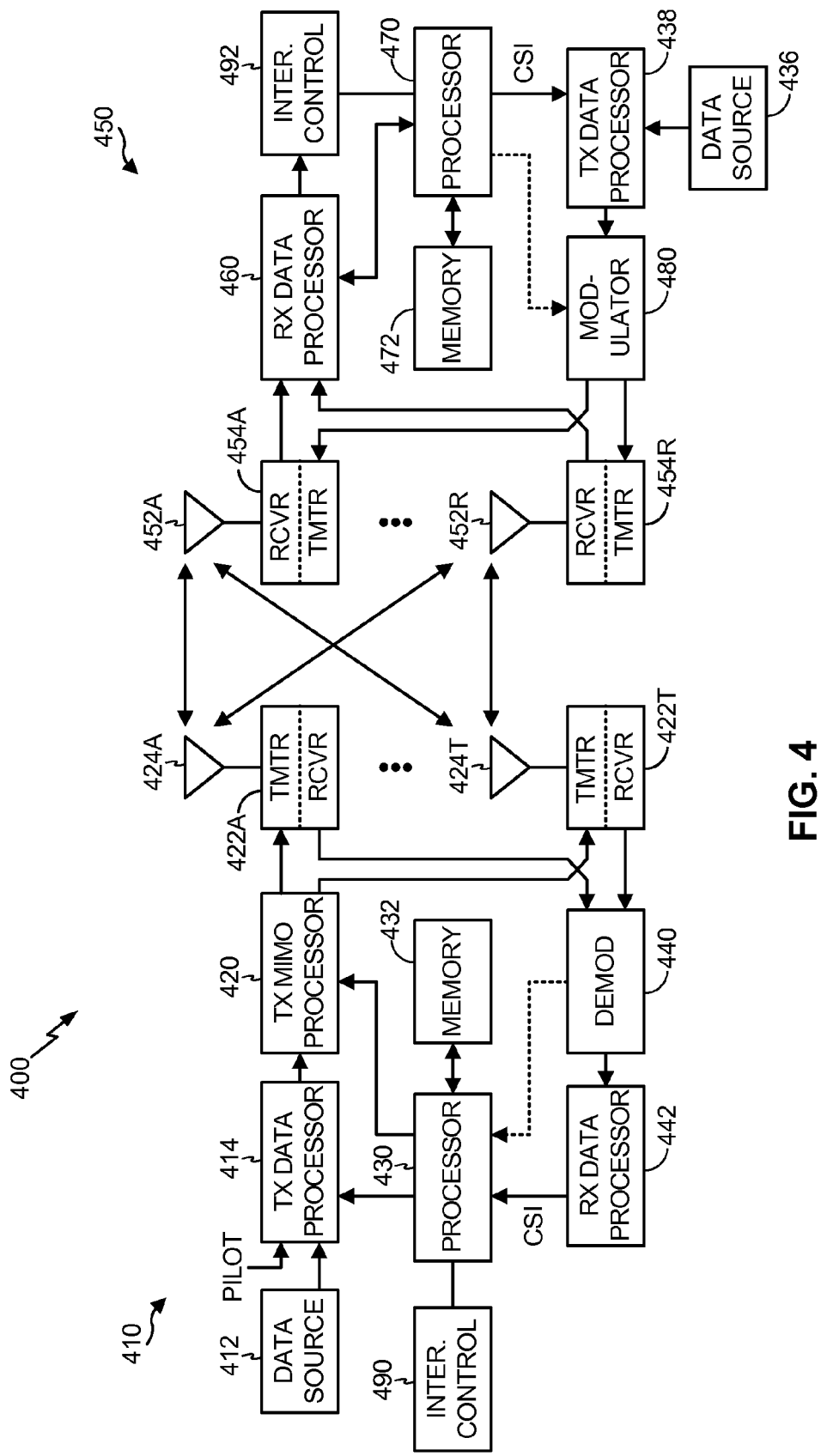
FIG. 4 is a functional block diagram of an exemplary femto node and an exemplary user equipment in one of the communication networks of FIG. 2.

The teachings herein may be incorporated into a device (e.g., a node, a user equipment, etc.) employing various components for communicating with at least one other device. FIG. 4 is a functional block diagram of a first exemplary femto node 410 and a first exemplary user equipment 450 in one of the communication networks of FIG. 2. As shown, a MIMO system 400 comprises a femto node 410 and a user equipment 450 (e.g., the UE 222). At the femto node 410, traffic data for a number of data streams is provided from a data source 412 to a transmit ("TX") data processor 414.

In one embodiment, each data stream is transmitted over a respective transmit antenna. The TX data processor 414 formats, codes, and interleaves the traffic data for each data stream based on a particular coding scheme selected for that data stream to provide coded data.

The coded data for each data stream may be multiplexed with pilot data using OFDM techniques. The pilot data is typically a known data pattern that is processed in a known manner and may be used at the receiver system to estimate the channel response. The multiplexed pilot and coded data for each data stream is then modulated (i.e., symbol mapped) based on a particular modulation scheme (e.g., BPSK, QSPK, M-PSK, or M-QAM) selected for that data stream to provide modulation symbols. The data rate, coding, and modulation for each data stream may be determined by instructions performed by a processor 430. A data memory 432 may store program code, data, and other information used by the processor 430 or other components of the femto node 410.

The modulation symbols for all data streams are then provided to a TX MIMO processor 420, which may further process the modulation symbols (e.g., for OFDM). The TX MIMO processor 420 then provides NT modulation symbol streams to NT transceivers ("XCVR") 422A through 422T. In some aspects, the TX MIMO processor 420 applies beam-forming weights to the symbols of the data streams and to the antenna from which the symbol is being transmitted.

Each transceiver 422 receives and processes a respective symbol stream to provide one or more analog signals, and further conditions (e.g., amplifies, filters, and upconverts) the analog signals to provide a modulated signal suitable for transmission over the MIMO channel. NT modulated signals from transceivers 422A through 422T are then transmitted from NT antennas 424A through 424T, respectively.

At the femto node 450, the transmitted modulated signals are received by NR antennas 452A through 452R and the received signal from each antenna 452 is provided to a respective transceiver ("XCVR") 454A through 454R. Each transceiver 454 conditions (e.g., filters, amplifies, and downconverts) a respective received signal, digitizes the conditioned signal to provide samples, and further processes the samples to provide a corresponding "received" symbol stream.

A receive ("RX") data processor 460 then receives and processes the NR received symbol streams from NR transceivers 454 based on a particular receiver processing technique to provide NT "detected" symbol streams. The RX data processor 460 then demodulates, deinterleaves, and decodes each detected symbol stream to recover the traffic data for the data stream. The processing performed by the RX data processor 460 is complementary to that performed by the TX MIMO processor 420 and the TX data processor 414 at the femto node 410.

A processor 470 periodically determines which pre-coding matrix to use (discussed below). The processor 470 formulates a reverse link message comprising a matrix index portion and a rank value portion. A data memory 472 may store program code, data, and other information used by the processor 470 or other components of the femto node 450.

The reverse link message may comprise various types of information regarding the communication link and/or the received data stream. The reverse link message is then processed by a TX data processor 438. The TX data processor 438 also receives traffic data for a number of data streams from a data source 436. The modulator 480 modulates the data streams. Further, the transceivers 454A through 454R condition the data streams and transmits the data streams back to the femto node 410.

At the femto node 410, the modulated signals from the femto node 450 are received by the antennas 424. Further, the transceivers 422 condition the modulated signals. A demodulator ("DEMOD") 440 demodulates the modulated signals. A RX data processor 442 processes the demodulated signals and extracts the reverse link message transmitted by the femto node 450. The processor 430 then determines which pre-coding matrix to use for determining the beam-forming weights. Further, the processor 430 processes the extracted message.

Further, the femto node 410 and/or the femto node 450 may comprise one or more components that perform interference control operations as taught herein. For example, an interference ("INTER") control component 490 may cooperate with the processor 430 and/or other components of the femto node 410 to send/receive signals to/from another device (e.g., femto node 450) as taught herein. Similarly, an interference control component 492 may cooperate with the processor 470 and/or other components of the femto node 450 to send/receive signals to/from another device (e.g., femto node 410). It should be appreciated that for each femto node 410 and 450 the functionality of two or more of the described components may be provided by a single component. For example, a single processing component may provide the functionality of the interference control component 490 and the processor 430. Further, a single processing component may provide the functionality of the interference control component 492 and the processor 470.

Figure 5:
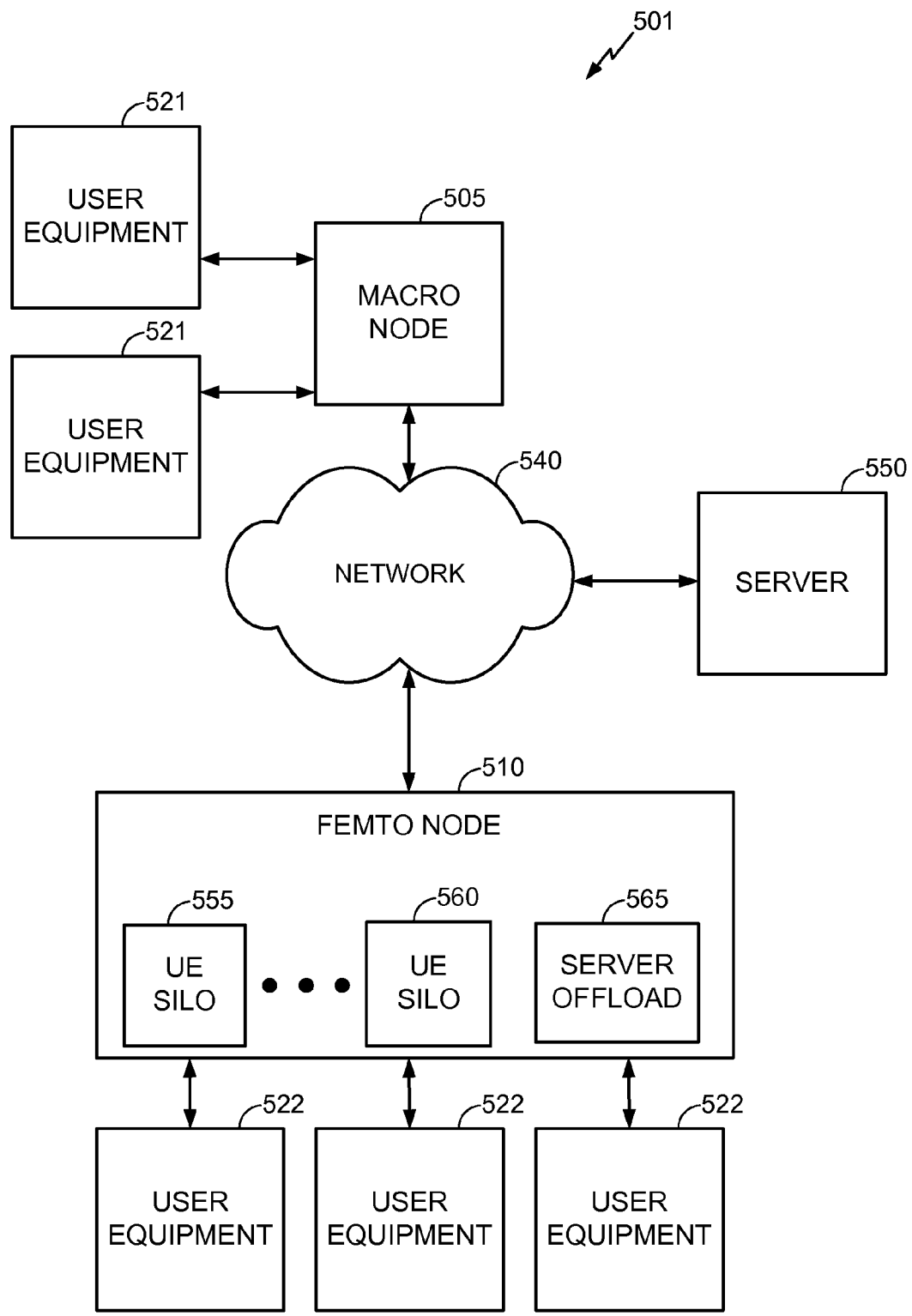
FIG. 5 illustrates additional exemplary operations of a communication network.

FIG. 5 illustrates additional exemplary operations of a communication network 501. The communication network 501 comprises a femto node 510. The femto node 510 may be similar to the femto node 210 of FIG. 2. As described above, the femto node 510 may provide communication access for one or more user equipment (UE), such as one or more UE 522. In one embodiment, the UE 522 and the femto node 510 may communicate directly by wireless communication. The femto node 510 is communicatively coupled to a network 540. In one embodiment, the femto node 510 is connected to the network 540 by a wired connection. The network 540 may be similar to the network 240 of FIG. 2. In one embodiment, the network 540 may be a public network such as the internet. In other embodiments, the network 540 may be a private network or a combination of public and private networks. By communicating through network 540, the femto node 510 may communicate with a server 550. The server 550 may offer services or store content for use by the UEs 522 and 521. The femto node 510 may also communicate with a macro node, such as the macro node 505. The macro node 505 may be similar to the macro node 205 of FIG. 2. The macro node 505 may provide communication coverage for one or more additional UEs, such as one or more UE 521. Thus, while the UE 522, may communicate directly with the femto node 510, the UE 521 may communicate with the femto node 510 indirectly via the macro node 505 and the network 540.

In some embodiments, it is desirable for the UE 522 to be able to offload or distribute some of its processing tasks. In general, offloading a task or distributed computing refers to a process by which multiple entities cooperate to perform a function. Where one device is constrained in terms of resources such as power or computing capability, offloading certain tasks can increase the functional capabilities of the device. For example, the battery life of the UE 522 may be limited such that power intensive computational operations can not be performed indefinitely. Thus, offloading a task can advantageously extend the battery life of the UE 522. Alternatively, limitations on the computing power in terms of operations per second or types of operations may constrain speed or accuracy of certain calculations. Thus, offloading a task can advantageously allow the UE 522 to quickly obtain results without requiring hardware capability or power for quickly generating the results.

In one aspect, the femto node 510 is used for offloading processing tasks from the UEs 521 and 522. For example, the UE 522 may supply the femto node 510 with data and with an instruction to perform certain operations on the data. The femto node 510 may perform the operations and return the result to the UE 522. In this manner, the UE 522 is able to conserve the power or other resources that would have been consumed by performing the operations at the UE 522. In another example, the femto node 510 may receive communications from the network 540 for the UE 522. However, rather than passing the communications on to the UE 522, the femto node may perform a processing task on the communications. For example, the femto node 510 may be configured to filter out irrelevant communications rather than passing them along. In this manner, the band width and power associated with receiving irrelevant communications are saved by the UE 522. In addition, the UE conserves the resources that would have been spent determining which communications were irrelevant. In general, the femto node 510 may advantageously be treated as an extension of the UE 522. Thus, the UE 522 may be configured to access the relatively abundant processing and power resources of the femto node 510. Examples describing distributed processing between the femto node 510 and the UEs 521 and 522 are described below in greater.

In one aspect, the femto node 510 may be treated as a trusted extension of the UEs 521 and 522. For example, the femto node 510 may be used to store data corresponding to users of the UEs 521 and 522 such as preferences, transactions histories, or profiles. Based on the stored information, the femto node 510 may be able to better perform processing tasks on behalf of the UEs 521 and 522. Advantageously, the femto node 510 may be able to utilize the stored information without exposing or providing the information directly to other devices such as the server 550. In this manner, the femto node 510 can offer enhanced functionality without compromising privacy or security. In one embodiment, the information regarding each UE 521 and 522 is logically separated on the femto node 510 into a corresponding UE silo, e.g., the silos 555, and 560. In this manner, the information corresponding to each UE 521 and 522 can be kept separate and secure. In other embodiments, the femto node 510 may also comprise offload resources 565 for one or more servers 550.

In one aspect, for example due to privacy and security concerns, the UEs 521 and 522 do not assign processing tasks to untrusted nodes. A trust relationship may be created between the UEs 521, 522 and a node through the exchange of credential information of the subscriber. Such a trust relationship is formed between a UE 521 and the femto node 510 during registration of the UE 521 with the femto node 510. For example, a trust relationship is formed between a UE 521 and the femto node 510 when the UE 521 registers to communicate with the femto node 510 and the UE 521 shares credential information related to its current communication with the macro node 505 that communicates over the same network 540 as the femto node. The UE 521 using the femto node 510 is authenticated and authorized to use the services that the femto node provides, while the UE 521 is also assured that the femto node's identity and integrity are credible. The UE 521 and the femto node 510 may further use encryption mechanisms for secure communications.

There are several reasons a trust relationship should exist between the UE 521 and the femto node 510. For example, when the femto node 510 receives a processing task, it should be able to verify the identity of the UE 521 assigning the task; else the femto node 510 could receive malicious requests from unknown sources. Further, the UE 521 and the femto node 510 should be able to securely exchange communications to avoid eavesdropping.

In another aspect, the femto node 510 is used for offloading processing tasks from the server 550. In one embodiment, the server 550 may communicate with the femto node 510 and request that the femto node 510 perform a service that would otherwise have been performed by the server 550. For example, the server 550 may request that the femto node 510 periodically access a particular website in order to determine if any new content is available. The femto node 510 may perform the service and return the result to the UE 522 or to the server 550. In this manner, the server 550 is able to conserve the bandwidth and reduce load or other resources that would have been consumed by performing the service for the UE 521. This may be particularly advantageous where the server 550 is able to offload services for a large number of UEs to their respective femto nodes. Examples further describing distributed processing between the femto node 510 and the server 550 are described below in greater.

In one example, the femto node 510 may run applications on behalf of the UE 521 (e.g., pre-fetch e-mail/RSS feeds, etc.). Accordingly, the femto node 510 may exchange information with the UE 521 such as information regarding which items to pre-fetch. Further, the femto node 510 may act as a proxy for an account associated with a user of the application. Accordingly, the femto node 510 may create a transport layer security (TLS) session with a server 550 that provides the service (e-mail, RSS feeds, etc.) on behalf of the UE 521. Thus, any data from the server 550 is fetched by the femto node 510, which then sends the appropriate data to the UE 521. The femto node 510 may isolate the TLS sessions for each individual UE, and may have a different TLS session for each individual UE for security purposes. In another aspect, any secure session normally required between a UE 521 and the server 550 for an application may instead be formed only between the femto node 510 and the server 550. Communications between the UE 521 and the femto node 510 may instead rely on L2 security between the UE 521 and the femto node 510.

As stated above, the femto node 510 may serve as a content aware proxy for the UE 521. Based on the content of data received from the server 550, the femto node 510 may then process the data or send a portion or all of the data to the UE 521. For example, the femto node 510 may filter content received from the server 550 and only send information to the UE 521 that is relevant to a user of the UE 521. The filter may be based on a set of user profiles/preferences that defines what type of information is pertinent to the user. The user preferences may be sent form the UE 521 to the server 550. In one aspect, the femto node 510, based on the user preferences, communicates with one or more servers such as the server 550 to gather relevant information and transmit the information to the UE 521. For example, the user preferences may indicate a podcast, RSS feed, etc. of interest. The server 550 may gather the information from the relevant servers. The user preferences may further indicate what types of information is of interest to the user. The femto node 510 may gather information from various sources such as podcasts, RSS feeds, etc. and filter the information of relevance, and transmit only the relevant information to the UE 521.

In another aspect, advantageously, the femto node 510 may multiplex content across multiple UEs. For example if the same data is requested from the server 550 from multiple UEs, the femto node 510 may make a single request, and send the received data to the multiple UEs.

In yet another example, the femto node 510 may provide storage functions for the UE 521. For instance, the UE 521 may provide an index into a database that is identified by a global or domain-specific ID, and the database is stored in the femto node 510. Based on the index, the femto node 510 can write/read the relevant data and send/receive the data to/from the UE 521.

In another aspect, the femto node 510 allows for both Local IP access (LIPA) and Remote IP access (RIPA) from the UE 521 to the femto node 510. LIPA allows the UE 521 to communicate with the local area network that the femto node 510 resides in using an air interface (e.g., cdma2000, UMTS, LTE, etc.) between the femto node 510 and the UE 521. RIPA allows the UE 521 to have IP connectivity with such a local area network even where the connection between the UE 521 and the femto node 510 is indirect. Accordingly, LIPA and RIPA allow the UE 521 to communicate with the femto node 510, and any devices on the same local area network as the femto node 510, through either a direct or an indirect connection, respectively. Accordingly, the UE 521 may access a server or a workstation computer, for example, that is on the same local area network as the femto node 510. In one embodiment, the UE 521 may use such access to a server or a workstation computer to further offload processing tasks to such a server or workstation computer.

In another aspect, the femto node 510 allows for many-to-one, one-to-many, and many-to-many data communications and processing via the femto node 510. Accordingly, one or many nodes provide inputs for one or more tasks to the femto node 510 to be executed by the femto node 510. Further, one or many nodes receive outputs of the processed tasks from the femto node 510. In addition, one or more nodes that provide inputs to the femto node 510 can also receive the outputs. These nodes may be UEs (e.g., UEs 521 and 522) or server nodes (e.g., server 550). In some embodiments, some of the nodes may be remotely connected to the femto node 510 over RIPA (Remote IP Access). As an example of a one-to-many task, the UE 521 may request a recommendation for a movie for a family. The femto node 510 may then process the request while looking up the stored/learned user profiles for the members of the family, and present a recommendation for a movie to all the users in the family via one or more additional UEs. As another example of a one-to-many task, a server 550 may send a request to the femto node 510 to make such a movie recommendation on a Friday afternoon to the members of the family via one or more UEs 521 and/or UEs 522. As an example of a many-to-many task, the femto node 510 may check for the presence of a plurality of users in the home by noting that it is receiving inputs from a plurality of UEs 521, or inputs associated with body-area-network sensors that are communicating with the UEs 521 associated with the users. This allows the femto node 510 to check for the presence information of multiple users in the home, and then provide an update regarding such presence information to all users in the family via the plurality of UEs 521. In addition, as an example of a many-to-one task or a many-to-many task, based on the reception of presence information inputs of family members in the home, the femto node 510 can make a recommendation for a restaurant for dinner to one of the family members or all of the family members via one or more UEs 521, based on the user profiles of the family members, and known promotions (stored at the femto node 510 and obtained from a targeted content message provider) from restaurants near the home.

In other aspects, the femto node 510 may be a smart-grid gateway communicating with a smart meter and with smart devices/smart plugs within the home. The femto node 510 may also communicate with the homeowner(s) or user(s) over WWAN (local user) or over RIPA (remote user). If, for example, the utility company wants to turn off the air-conditioning (AC) or the dryer for a demand-response scenario, it could instruct the femto node 510 to turn off the AC/dryer. However, the femto node 510 can ping the user over RIPA (if the user is remote), get the homeowner's approval (to check if someone is at home before turning off, such as a guest, family member, or relative), and then turn off the AC/dryer.

Figure 6:
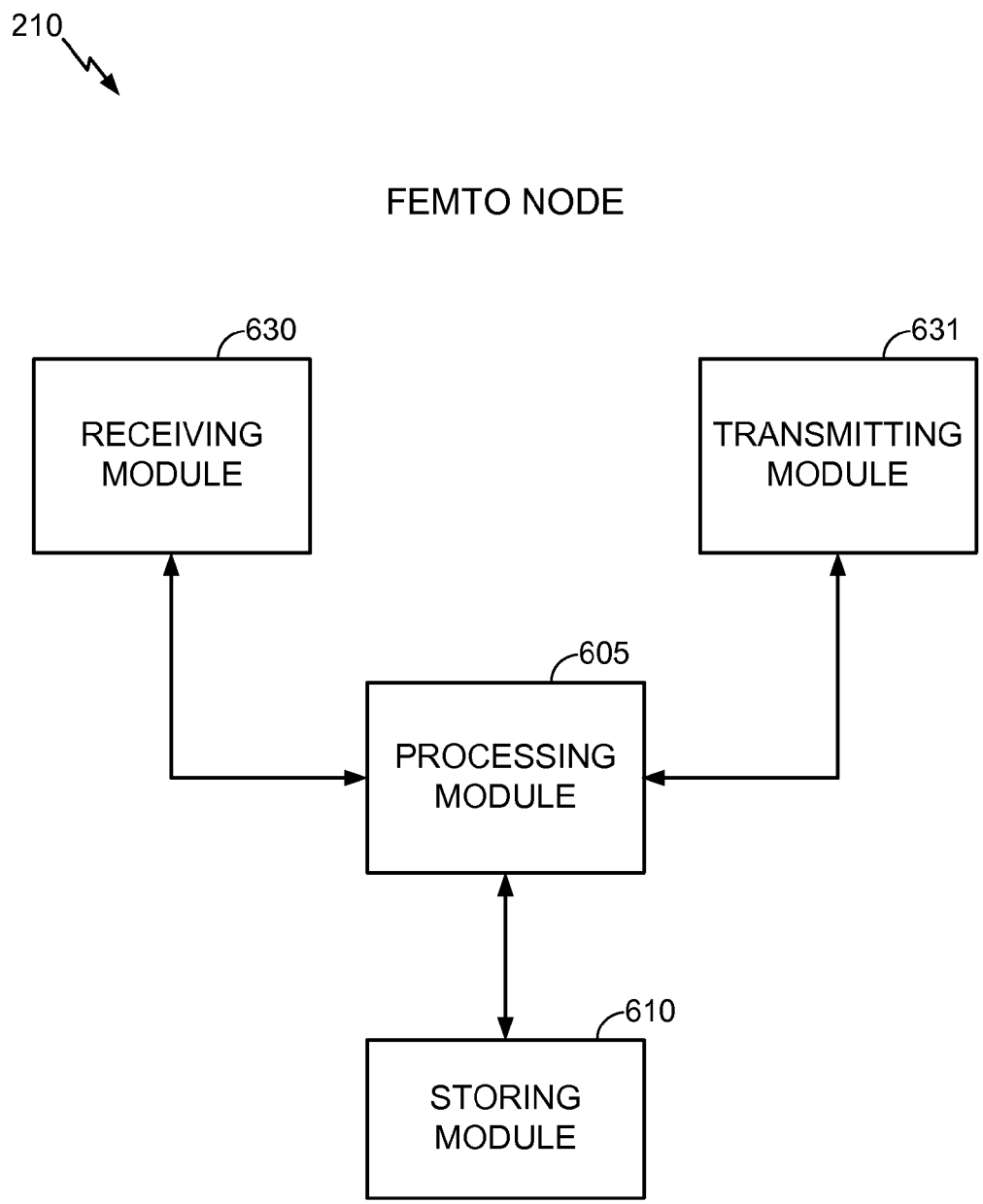
FIG. 6 is a functional block diagram of an exemplary femto node in the communication network of FIG. 5.

FIG. 6 is a functional block diagram of an exemplary femto node 210 in the communication network of FIG. 5. The femto node 210 may be similar to the femto node 510 of FIG. 5. The femto node 210 may comprise a transmitting module 631. The transmitting module 631 may transmit outbound messages to other devices, such as, for example, the UE 522 and the network 540 of FIG. 5. The messages may include communications related to distributed computing with the UE 522. For example, the messages may include the results of processing tasks offloaded by the UE 522. Femto node 210 may also comprise a receiving module 630 configured to receive inbound messages from devices such as the UE 522 and the network 540. The received messages may include instructions from the UE 522 to perform a processing task or data from the network 540 to be processed. The receiving module 630 and the transmitting module 631 may be coupled to a processing module 605. The receiving module 630 may pass an inbound message to the processing module 605 for processing. The processing module 605 may process and pass an outbound message to the transmitting module 631 for transmission. The processing module 605 may be configured to process the inbound and outbound wired and wireless messages via the receiving module 630 and the transmitting module 631. The processing module 605 may also be configured to control other components of the femto node 210.

The processing module 605 may further be coupled, via one or more buses, to a storing module 610. The processing module 605 may read information from or write information to the storing module 610. For example, the storing module 610 may be configured to store inbound our outbound messages before, during, or after processing. In particular, the storing module 610 may be configured to store information relating process offloading. In one aspect, the storing module 610 may also be configured to store information related to a processing task that has been offloaded from the UE 522.

The receiving module 630 and the transmitting module 631 may comprise an antenna and a transceiver. The transceiver may be configured to modulate/demodulate the wireless outbound/inbound messages. The wireless outbound/inbound messages may be transmitted/received via the antenna. The antenna may be configured to send and/or receive the outbound/inbound wireless messages over one or more channels. The receiving module 630 may demodulate the data received. The transmitting module 631 may modulate data to be sent from the femto node 210. The processing module 605 may provide data to be transmitted.

The receiving module 630 and the transmitting module 631 may further comprise a modem. The modem may be configured to modulate/demodulate the outbound/inbound wired messages going to or coming from the network 540. The receiving module 630 may demodulate data received. The demodulated data may be transmitted to the processing module 605. The transmitting module 631 may modulate data to be sent from the femto node 210. The processing module 605 may provide data to be transmitted.

The storing module 610 may comprise processing module cache, including a multi-level hierarchical cache in which different levels have different capacities and access speeds. The storing module 610 may also comprise random access memory (RAM), other volatile storage devices, or non-volatile storage devices. The storage may include hard drives, optical discs, such as compact discs (CDs) or digital video discs (DVDs), flash memory, floppy discs, magnetic tape, and Zip drives.

Although described separately, it is to be appreciated that functional blocks described with respect to the femto node 210 need not be separate structural elements. For example, the processing module 605 and the storing module 610 may be embodied in a single chip. The processing module 605 may additionally, or in the alternative, contain memory, such as registers. Similarly, one or more of the functional blocks or portions of the functionality of various blocks may be embodied in a single chip. Alternatively, the functionality of a particular block may be implemented on two or more chips.

One or more of the functional blocks and/or one or more combinations of the functional blocks described with respect to the femto node 210, such as the processing module 605, may be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. One or more of the functional blocks and/or one or more combinations of the functional blocks described with respect to the femto node 610 may also be implemented as a combination of computing devices, e.g., a combination of a DSP and a microprocessor, a plurality of microprocessors, one or more microprocessors in conjunction with a DSP communication, or any other such configuration.

Figure 7A:
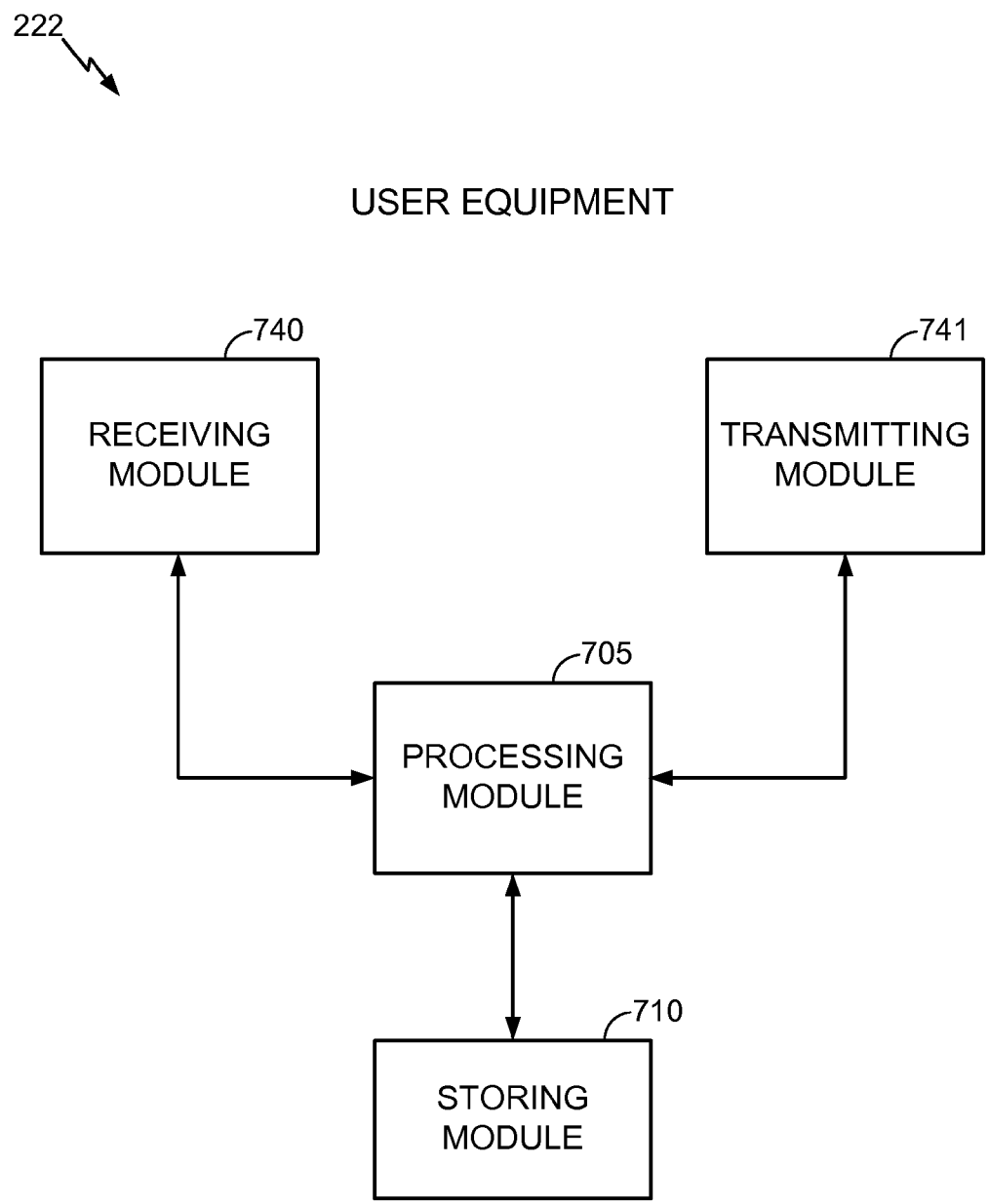
FIG. 7A is a functional block diagram of an exemplary user equipment in the communication network of FIG. 5.

FIG. 7A is a functional block diagram of an exemplary UE 222 in the communication network of FIG. 5. The UE 222 may be similar to the UE 522 of FIG. 5. The UE 222 may comprise a transmitting module 741. The transmitting module 741 may transmit outbound messages to other devices, such as, for example, the femto node 510. The messages may include information related to offloading processing tasks. For example, the messages may include an indication of an operation to be performed. The messages may also include data to be processed. The UE 222 may also comprise a receiving module 740 configured to receive inbound messages from devices such as the femto node 510. The receiving module may be configured to receive message related to off loading processing. For example, the messages may include the results off processing tasks that were offloaded to the femto node 510. The receiving module 740 and the transmitting module 741 may be coupled to a processing module 705. The receiving module 740 may pass an inbound message to the processing module 705 for processing. The processing module 705 may process and pass an outbound message to the transmitting module 741 for transmission. The processing module 705 may also be configured to control other components of the UE 221.

The processing module 705 may further be coupled, via one or more buses, to a storing module 710. The processing module 705 may read information from or write information to the storing module 710. For example, the storing module 710 may be configured to store inbound our outbound messages before, during, or after processing. In particular, the storing module 710 may be configured to store information relating process offloading.

The receiving module 740 and the transmitting module 741 may comprise an antenna and a transceiver. The transceiver may be configured to modulate/demodulate the wireless outbound/inbound messages going to or coming from local network device 540 or another UE. The wireless outbound/inbound messages may be transmitted/received via the antenna. The antenna may be configured to send and/or receive the outbound/inbound wireless messages over one or more channels. The receiving module 730 may demodulate the data received. The transmitting module 731 may modulate data to be sent from the UE 222. The processing module 705 may provide data to be transmitted.

The storing module 710 may comprise processing module cache, including a multi-level hierarchical cache in which different levels have different capacities and access speeds. The storing module 710 may also comprise random access memory (RAM), other volatile storage devices, or non-volatile storage devices. The storage may include hard drives, optical discs, such as compact discs (CDs) or digital video discs (DVDs), flash memory, floppy discs, magnetic tape, and Zip drives.

Although described separately, it is to be appreciated that functional blocks described with respect to the UE 222 need not be separate structural elements. For example, the processing module 705 and the storing module 710 may be embodied in a single chip. The processing module 705 may additionally, or in the alternative, contain memory, such as registers. Similarly, one or more of the functional blocks or portions of the functionality of various blocks may be embodied in a single chip. Alternatively, the functionality of a particular block may be implemented on two or more chips.

One or more of the functional blocks and/or one or more combinations of the functional blocks described with respect to the UE 222, such as the processing module 705, may be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. One or more of the functional blocks and/or one or more combinations of the functional blocks described with respect to the femto node 710 may also be implemented as a combination of computing devices, e.g., a combination of a DSP and a microprocessor, a plurality of microprocessors, one or more microprocessors in conjunction with a DSP communication, or any other such configuration.

Figure 7B:
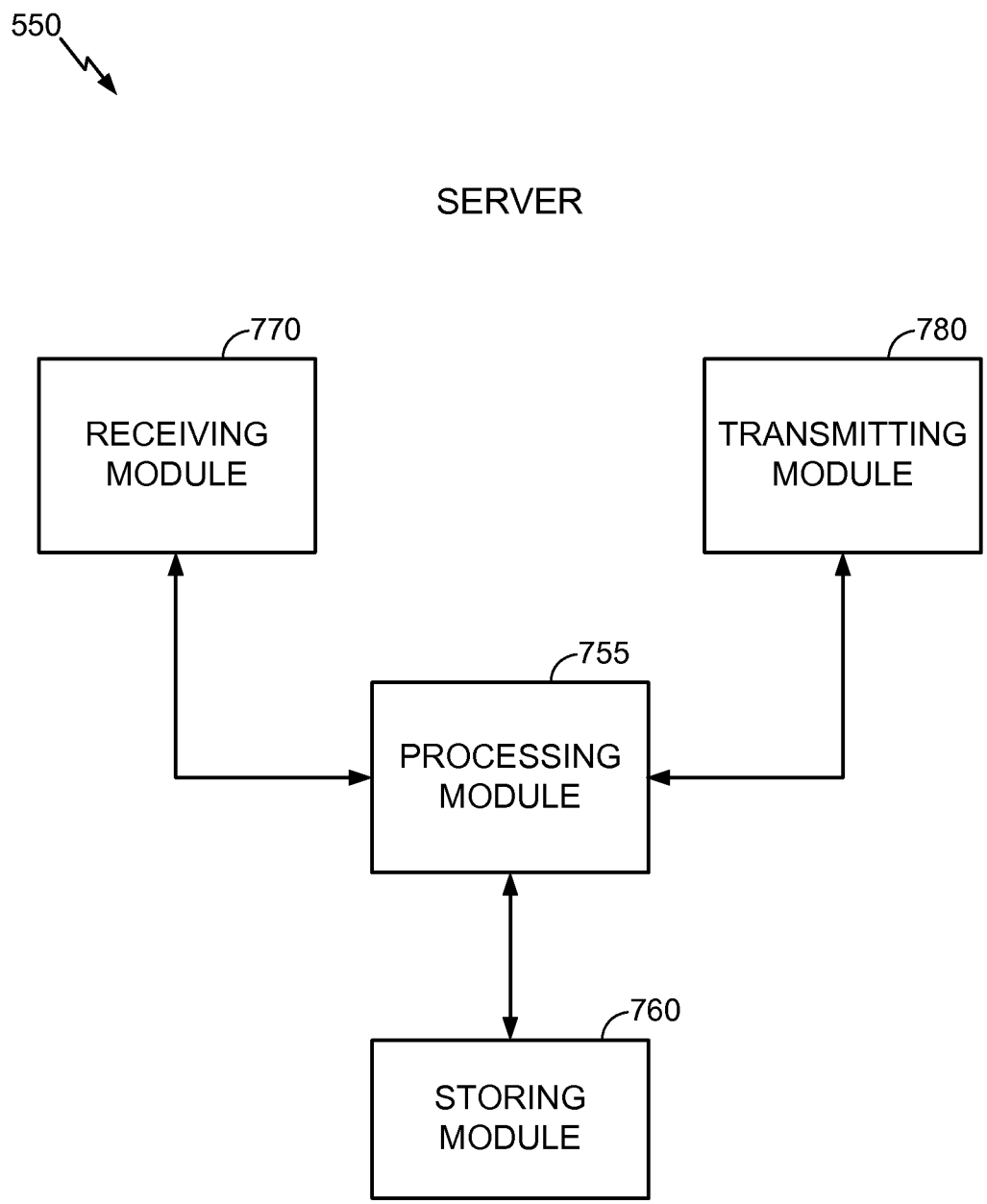
FIG. 7B is a functional block diagram of an exemplary server in the communication network of FIG. 5.

FIG. 7B is a functional block diagram of an exemplary server 550 in the communication network of FIG. 5. The server 550 may be similar to the server 550 of FIG. 5. The server 550 may comprise a transmitting module 780. The transmitting module 780 may transmit outbound messages to other devices, such as, for example, the femto node 510. The messages may include information related to offloading processing tasks. For example, the messages may include an indication of an operation to be performed. The messages may also include data to be processed. The server 550 may also comprise a receiving module 770 configured to receive inbound messages from devices such as the femto node 510. The receiving module may be configured to receive message related to off loading processing. For example, the messages may include the results off processing tasks that were offloaded to the femto node 510. The receiving module 770 and the transmitting module 780 may be coupled to a processing module 755. The receiving module 770 may pass an inbound message to the processing module 755 for processing. The processing module 755 may process and pass an outbound message to the transmitting module 780 for transmission. The processing module 755 may also be configured to control other components of the server 550.

The processing module 755 may further be coupled, via one or more buses, to a storing module 760. The processing module 755 may read information from or write information to the storing module 760. For example, the storing module 760 may be configured to store inbound our outbound messages before, during, or after processing. In particular, the storing module 760 may be configured to store information relating process offloading.

The receiving module 770 and the transmitting module 780 may comprise a modem. The modem may be configured to modulate/demodulate the outbound/inbound wired messages going to or coming from the network 540. The receiving module 770 may demodulate data received. The demodulated data may be transmitted to the processing module 755. The transmitting module 780 may modulate data to be sent from the server 550. The processing module 755 may provide data to be transmitted.

The storing module 760 may comprise processing module cache, including a multi-level hierarchical cache in which different levels have different capacities and access speeds. The storing module 760 may also comprise random access memory (RAM), other volatile storage devices, or non-volatile storage devices. The storage may include hard drives, optical discs, such as compact discs (CDs) or digital video discs (DVDs), flash memory, floppy discs, magnetic tape, and Zip drives.

Although described separately, it is to be appreciated that functional blocks described with respect to the server 550 need not be separate structural elements. For example, the processing module 755 and the storing module 760 may be embodied in a single chip. The processing module 755 may additionally, or in the alternative, contain memory, such as registers. Similarly, one or more of the functional blocks or portions of the functionality of various blocks may be embodied in a single chip. Alternatively, the functionality of a particular block may be implemented on two or more chips.

One or more of the functional blocks and/or one or more combinations of the functional blocks described with respect to the server 550, such as the processing module 755, may be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. One or more of the functional blocks and/or one or more combinations of the functional blocks described with respect to the femto node 760 may also be implemented as a combination of computing devices, e.g., a combination of a DSP and a microprocessor, a plurality of microprocessors, one or more microprocessors in conjunction with a DSP communication, or any other such configuration.

Figure 8:
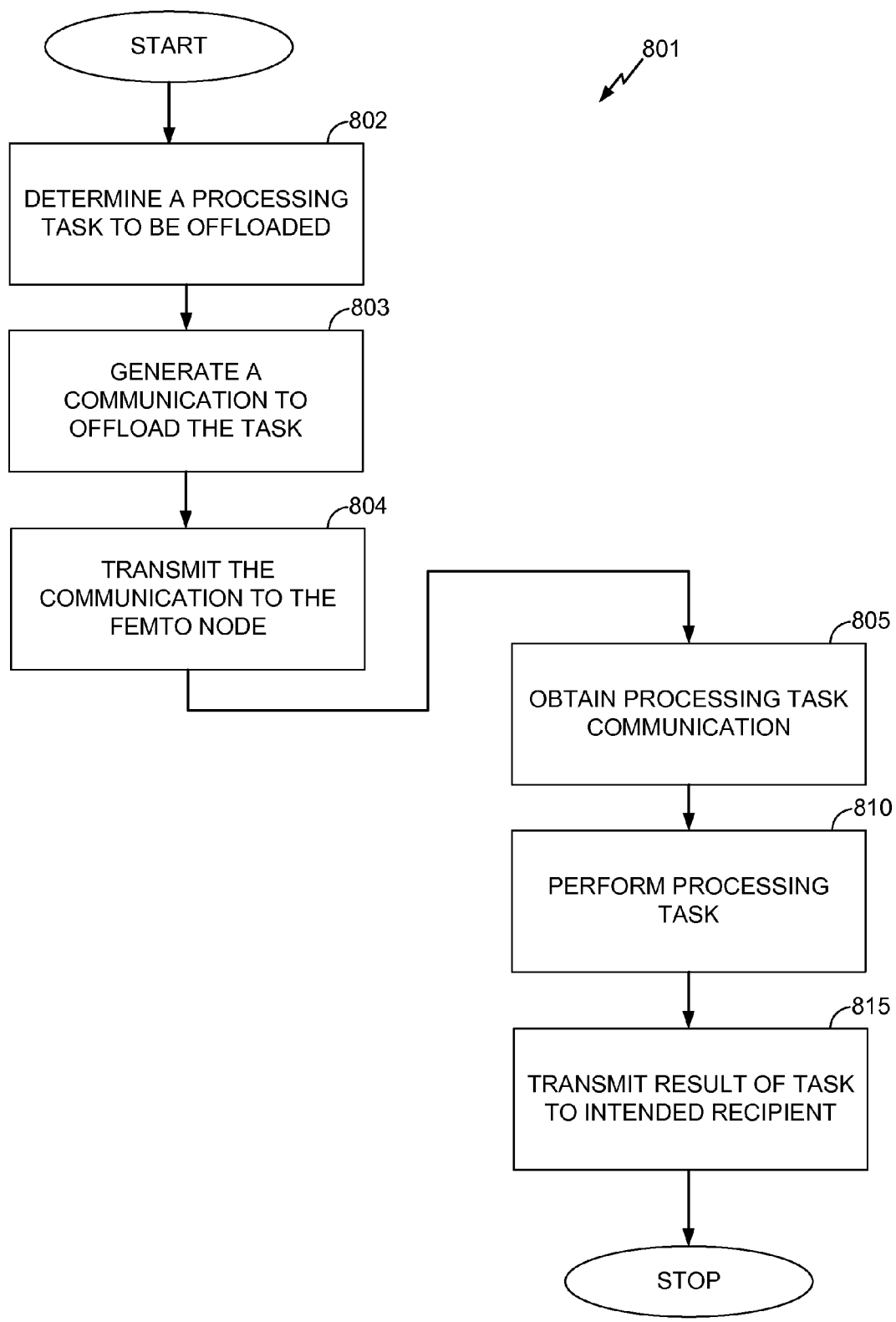
FIG. 8 is a flowchart illustrating an exemplary process of distributing processing between devices as shown in FIG. 5.

FIG. 8 is a flowchart illustrating an exemplary process 801 of distributing processing between devices as shown in FIG. 5. In one embodiment, the process 801 may be performed by a UE, such as the UEs 521 or 522 of FIG. 5, in conjunction with a femto node, such as the femto node 510 of FIG. 5. In another embodiment, the process 801 may be performed by a server, such as the server 550 of FIG. 5, in conjunction with the femto node 510. For ease of explanation, the process 801 will first be described with respect to the UE 522. At a step 802, the UE 522 determines a processing task to be offloaded. In general, it may be advantageous to offload a process where the cost of transmitting the request and receiving the response is lower than the cost of performing the task. Thus, for example, if the task to be offloaded is computationally simple, but involves significant amounts of data, the cost of sending the data to the femto node 510 to be processed and the cost of receiving the processed data may exceed the cost of performing the operation. In this case, the UE 522 may determine not to offload the task. In some embodiments, where the UE 522 is not capable of performing the processing task, the relative cost of communication is moot and the task may be offloaded. However, in such instances, using the femto node 510 to offload the task is advantageous because the latency of such communications is low and because the data transferred to the femto node 510 does not have to be exposed to the network 540 for processing. Thus the security and privacy of the data may be better maintained.

More generally, the allocation of tasks to different nodes can be based on factors such as the cost for communication of a message on a wireless link, the cost of computation of tasks on each node, i.e., the UE 522, femto node 510, and server 550, the relative amount of energies available on each node, their frequency of charging, the link conditions between the nodes, the bandwidth of a wireless channel, the interference on a wireless channel, the utilization factor of a channel, the number of nodes on a given channel, the wireless protocol being used for a given wireless link and the efficiency of the protocol, the degree of redundancy of information on the channel, a monetary cost of any for utilization of a link, and so on. Further, the decision to offload a task may be made dynamically based on current or previous conditions or statically based on the nature of the task to be offloaded or other factors. In one embodiment, determining a task to offload may comprise determining a resource saving value based on one or more of the factors described above. For example, the resource saving value may be an amount of energy that would be saved by offloading the task rather than performing the task locally at the UE 521 or server 550. The UE 521 and server 550 may compare the resource savings value to a threshold and decide to offload the task if the savings value exceeds the threshold.

Continuing to step 803, the UE 522 generates a communication to offload the task to the femto node 510. At step 804 the UE 522 transmits the communication to the femto node 510. As noted above, the steps 802, 803 and 804, may also be performed by the server 550. In some embodiments, the parameters considered by the server 550 when determining a process to offload may be different than those used by the UE 521. For example, the server 550 may be considered to have a relatively unlimited power supply, thus, available energy may not be as relevant. However, other factors such as bandwidth and load may be considered more relevant when determining processes or services to offload.

At a step 805, the femto node 510 obtains a processing task communication. For example, the UE 522 may establish communication with the femto node 510. The femto node 510 may use one or more security protocols to ensure that the UE 522 is authorized to communicate with the femto node 510. After establishing communication, the UE 522 may transmit a request to the femto node 510 to perform a processing task. Exemplary processing tasks may include, but are not limited to, encrypting or decrypting data, compressing or decompressing data, obtaining an encryption key pair, processing sensor data detected by the UE 522. Other examples include storing data transferred from the UE 522 or retrieving data from a server 550 via the network 540 and storing the retrieved data for later use. With some of these examples, the UE 522 may also provide data to the femto node 510 to process. In other examples, the femto node 510 may generate the data or may obtain the data from another device, such as the server 550, via the network 540. In some embodiments, the femto node 510 may be configured to wait for a period of time between obtaining the data and performing the requested processing task. In one embodiment, the UE 522 may transmit only an indication of a task to be performed. In this embodiment, the femto node 510 may be configured to determine the function to be performed based on the received indication. In another embodiment, the UE 522 may transmit specific instruction detailing the function to perform. These instructions may include, for example, computer executable instructions. In addition to identifying the task, the UE 522 may also indicate what is to be done with the result of the task. For example, the UE 522 may instruct the femto node 510 to store the result, to return the result to the UE 521, or to send the result to another device such as the UE 521 or the server 550. Further, more than one processing task may be received from one or more devices.

Continuing at step 810, the femto node 510 performs the requested processing task. As described above, the requested task may include retrieving data, storing data, transmitting data, processing data, or some combination thereof. Continuing at step 815, the femto node may transmit the results of the processing task to an intended recipient. For example, the femto node 510 may transmit the result of the task to the UE 522 or to another device such as the UE 521 or the server 550. In some embodiments, the result may be to transfer an uncompleted or partially completed task back to the UE 521 or the server 550. In some embodiments, the femto node 510 aggregates the results of multiple tasks and selectively transmits the aggregated result in an additional or alternative communication. The aggregated result may be transmitted at a time after the tasks are completed. In other embodiments, where the task does not generate a result, step 815 may be omitted. In other embodiments, step 815 may be performed selectively based on, for example, the type of processing task being performed. In other embodiments, the femto node 510 may be configured to wait for a period of time between performing the processing task and transmitting the results to an intended recipient.

Advantageously, the process 801 allows the UE 522 to make use of the processing and power resources available to the femto node 510. For example, in one embodiment, the UE 522 may comprise a sensor for detecting pressure that may be used to measure heart activity. The UE may record one of more waveforms indicative of heart activity via the sensor. However, the UE 522 may be constrained either by processing power or by battery life in its ability to analyze the waveforms. Thus, the UE 522 may send the waveforms to the femto node 510. The UE may request that the femto node 510 analyze the waveforms and that the femto node 510 send the results of the analysis to the UE 522 as well as to the UE 521 belonging to a medical practitioner. The femto node 510 may the process the waveforms and send the results to the requested devices. Advantageously, by using distributed computing, the UE 522 and femto node 510 are able to preserve the power and computing resources available to the UE 522. As described above, the process may also be used by the server 550 to distribute services amongst one or more femto nodes 510. For example, rather than providing the service directly to a plurality of UEs 521 and 522, the server 550 can offload some portion of its services to femto nodes 510 that are associated with the UEs 521 and 522. In this manner, the load on the server 550 can be reduced. In addition, in some embodiments, the latency of service can be reduced as well where the femto node 510 provides the service as the femto node 510 may have a shorter communication path with the femto node 521 as compared to the communication path between the UE 521 and the server 550.

Figure 9:
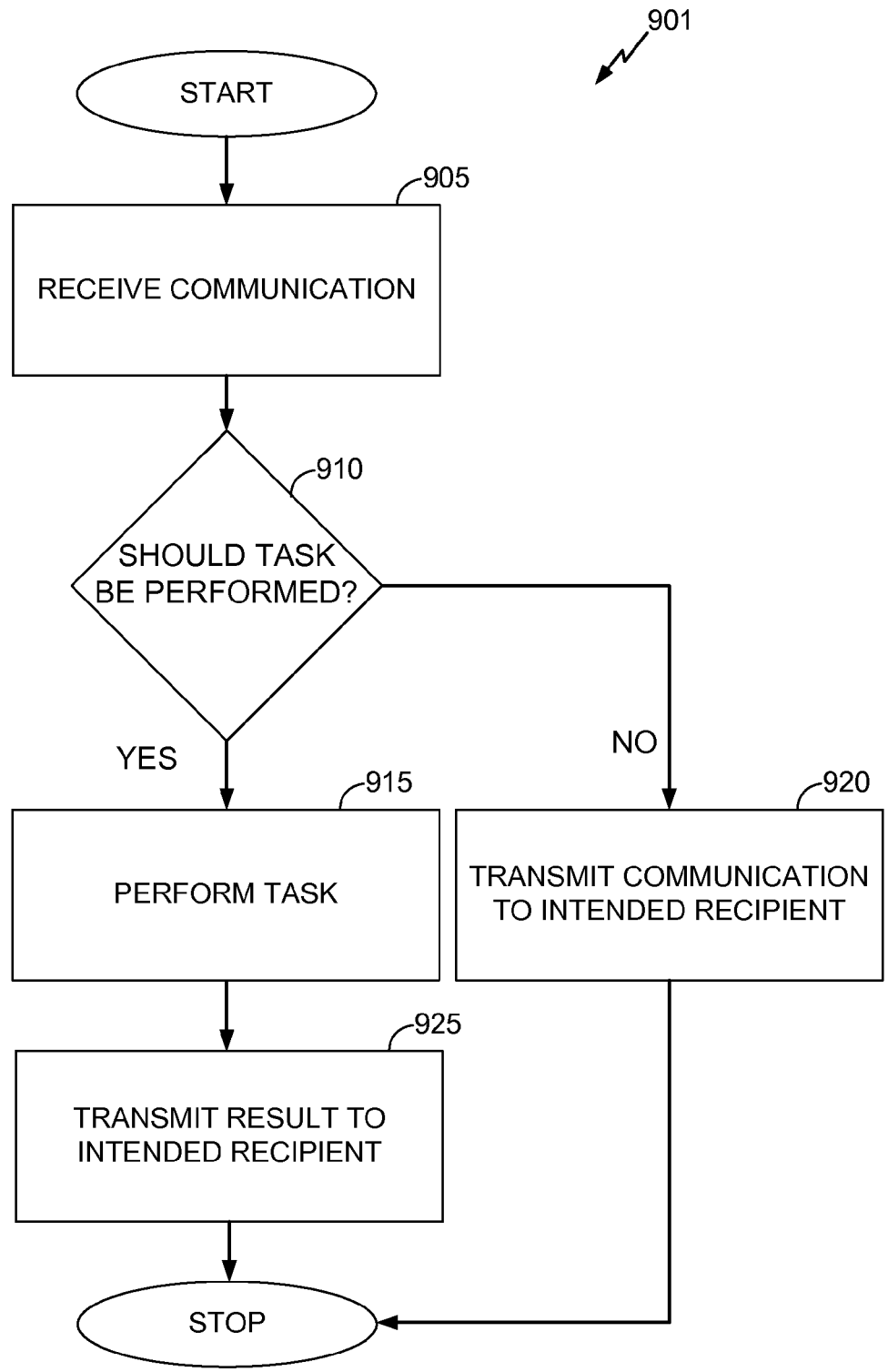
FIG. 9 is a flowchart illustrating another exemplary process of distributing processing between devices as shown in FIG. 5.

FIG. 9 is a flowchart illustrating an exemplary process 901 of distributing processing between wireless communication devices as shown in FIG. 5. As described above, a UE, such as the UE 521 or 522, may offload a processing task to a femto node, such as the femto node 510. Another type of distributed processing that may be implemented is processing of communications from the network 540 that are directed to the UE 522. This type of processing is illustrated by process 901 and may be performed by the femto node 510 in conjunction with the UE 522. At step 905, the femto node receives a communication from the network 540. The communication may be an unsolicited communication or it may be received in response to a prior communication from the femto node 510. For example, the femto node 510 may request and receive a media file, such as a video, from the server 550. Continuing at step 910, the femto node 501 determines if a processing task should be performed on the data in the communication. In one embodiment, the femto node 510 may determine whether a task should be performed based on the characteristics of the data and on a profile associated with the UE 522 or its user. For example, the femto node 510 may store information about the UE such as technical characteristics including about memory, processing capability, display characteristics, or other features. The profile may also include information about preferences of the user based on a history of interactions with the femto node 510. Based on the profile associated with the user and on the properties of the communication from the network, the femto node 510 can determine if any processing should be performed on the data in the communication. For example, if the communication includes a compressed media file, and the femto node 510 determines that the video will need to be decompressed in order to be displayed by the UE 522, the femto node 510 may decide to decompress the video before transmitting it to the UE 522. By doing so, the femto node can save the processing and power that would have been consumed by the UE 522 in decompressing the video. In another embodiment, the femto node 510 may determine whether or not to perform a task based on the communication and processing costs associated with performing and not performing the task. This decision process may be similar to the process described above with respect to step 802 for FIG. 8.

Continuing at step 915, if the femto node 510 determines that a processing task should be performed on the communication, the femto node 510 performs the processing task on the communication. At step 925, the femto node transmits the result of the task to the intended recipient, e.g., the UE 522. Returning to decision step 910, if the femto node 510 determines that no processing task should be performed on the communication, the femto node transmits the communication to the UE 522 as shown at step 920.

Advantageously, the present embodiments allow the femto node 510 to preserve the processing and power resources of the UE 522 by reducing the amount of processing done at the UE 522. However, in addition, the method 901 may be used to offload services from the network to the femto nodes as well. For example, network servers, such as the server 540 may periodically provide network service information to the femto node 510. This type of network information may include information on whitespace spectrum usage, base station identifiers in a particular area, or other information. When the femto node 510 receives these updates, it can store them. Later, when the UEs 510 need access to the network information, the UEs can get the information from the femto node 510 rather than from the server 540. From the UEs perspective, the distributed availability of such information can result in reduced latency when the information is requested because of the shorter communication path and the relative lack of congestion. Similarly, from the server's perspective, this distributed hosting of network service information can result in less congestion and asynchronous access requests.

Figure 10:
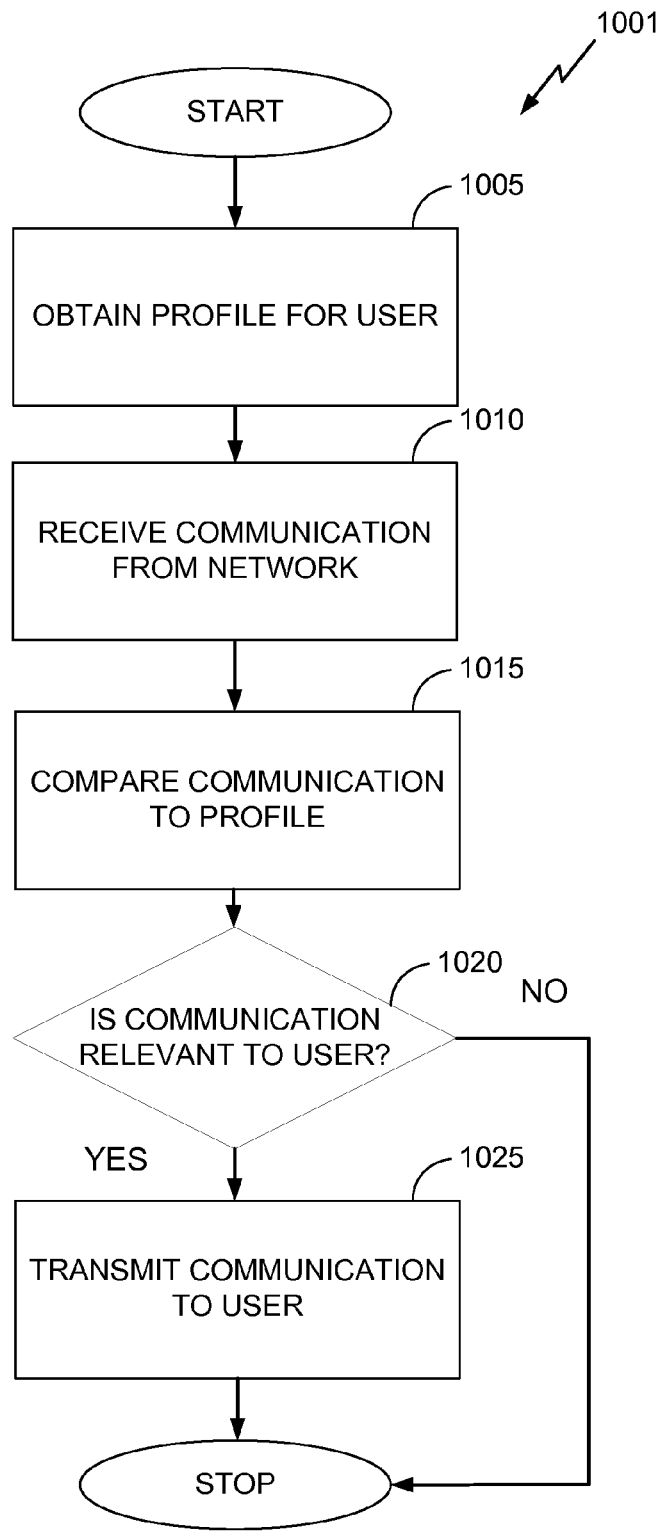
FIG. 10 is a flowchart illustrating another exemplary process of distributing processing between devices as shown in FIG. 5.

FIG. 10 is a flowchart illustrating another exemplary process 1001 of distributing processing between wireless communication devices as shown in FIG. 5. The process 1001 illustrates one particular example of a type of distributed processing where the femto node 510 acts as a filter for messages directed to the UE 522. At step 1005, the femto node obtains a profile for the UE 522 or its associated user. As noted above, the process of developing a user profile over time is perfectly suited for distributed computing. Over time, small, discrete amounts of information representative of user information such as preferences, locations, or other features can be transmitted to or recorded by the femto node 510. While any individual input may be relatively small, the processing capability, power, and storage required to track the development of a user model over time may be significant. Thus, the tracking of the user model can be done on the femto node 510 where resources are these resources are relatively more abundant. In addition, because the user profile is stored on the femto node 510 and not on the UE 522, when the UE 522 ceases to function, e.g., is lost, or replaced, the user profile persists and can be further developed rather than having to be started again from scratch. Advantageously, the user model aggregated over time may provide significant insight into the patterns and preferences of the user.

Such a user model can consist of many learned aspects of a user as a function of time based on user behavior. A predictive state machine can be developed to suggest one or more future locations with differing probability as a function of time based on learning user movement. This can be used to determine information that would be relevant, such as coupon related to a restaurant near location at a future time.

The relevant keywords for a user from a dictionary of keywords can be learned over a function of time based on user behavior. User keywords can be learned separately for different profiles (news, music, purchasing) of the user. This can be used to filter targeted content messages or ads relevant for a user, download podcasts and create customized content for a user. Complex data mining techniques could be used on the femto node 510 based on principal component analysis techniques, support-vector machine techniques or kernel regression techniques to determine and refine a user model as a function of time, and to determine/predict relevant information for the user based on a learned model. It may be difficult and computationally expensive to execute such algorithms on the UE 521.

The femto node 510 as a trusted extension of the UE 521, can store past user behavior, apply complex learning algorithms, and continuously refine the user model. Such user models can also be provided in full or in part by the user of the UE 521 to enable the femto node 510 to perform processing on behalf of the user. Additionally, a user model can persist in the femto node 510 even if user replaces equipment so that the user model is not lost if the UE 521 used by a user is replaced.

Continuing to step 1010, the femto node 510 receives a communication from the network 540. In one embodiment, the communication may comprise a targeted content message (TCM) or advertisement. These TCMs may be unsolicited or may correspond to previous communications from the UE 522 over the network 540. Continuing at step 1015, the femto node 510 compares the communication to the profile for the UE 522 and its user in order to determine the relevancy of the communication. As noted above, the user profile may comprise information on preferences of the user of the UE 522. In another embodiment, the profile may comprise actual or predicted location information based on the profile or on communications from the UE 522. The predicted location may be further based on the time, where different locations are predicted for different times. The femto node 510 may be configured to determine a degree of relevance of the communication based on the data in the communication and the data in the profile. For example, if the profile indicates that the user is or is likely to be in a certain location at some time point (which may be a time point in the future from when the communication is received), the femto node may determine that communications pertaining to stores or events in proximity to the location are more relevant. Alternatively, the message may have to do with a particular product and the femto node 510 may determine a degree of relevance based on the personal preferences in the profile.

Continuing to decision step 1020, the femto node 510 determines if the communication is sufficiently relevant to the user of the UE 522. For example, the femto node 510 may compare the degree of relevance to a threshold. If the degree of relevance exceeds the threshold, the femto node 510 may determine that the communication is sufficiently relevant. In this case, the method 1001 proceeds to step 1025 and the femto node transmits that communication to the UE 522. Returning to decision step 1020, if the message is not sufficiently relevant, the message is not forwarded and the method 1001 concludes. Advantageously, the present method facilitates significant power savings for the UE 522 by not having to receive or process irrelevant communications. In addition, a sophisticated user model describing the user of the UE 522 can be developed without excessive processing by the UE 522.

Figure 11:
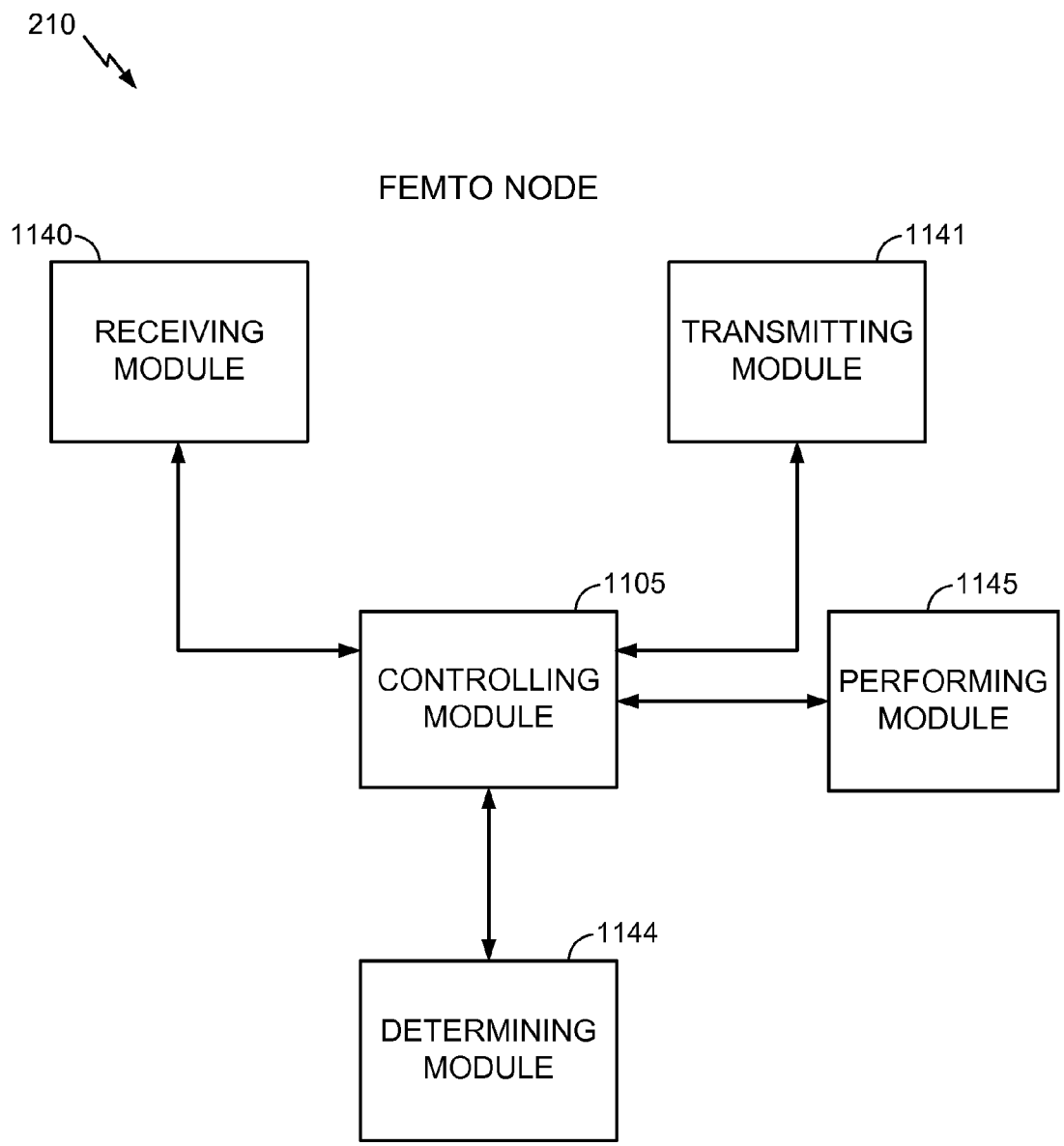
FIG. 11 is a functional block diagram of an exemplary femto node in the communication network of FIG. 5.

FIG. 11 is a functional block diagram of an exemplary femto node in the communication network of FIG. 5. As shown, the femto node 210 may comprise a controlling module 1105, a receiving module 1140, a transmitting module 1141, a performing module 1145, and a determining module 1144. The controlling module 1105 may correspond at least in some aspects to, for example, a processor or a processing module as discussed herein. The receiving module 1140 may correspond at least in some aspects to, for example, a receiver or a receiving module as discussed herein. The transmitting module 1141 may correspond at least in some aspects to, for example, a transmitter or a transmitting module as discussed herein. The performing module 1145 may correspond at least in some aspects to, for example, a processor or a processing module as discussed herein. The determining module 1144 may correspond at least in some aspects to, for example, a processor or a processing module as discussed herein.

Figure 12:
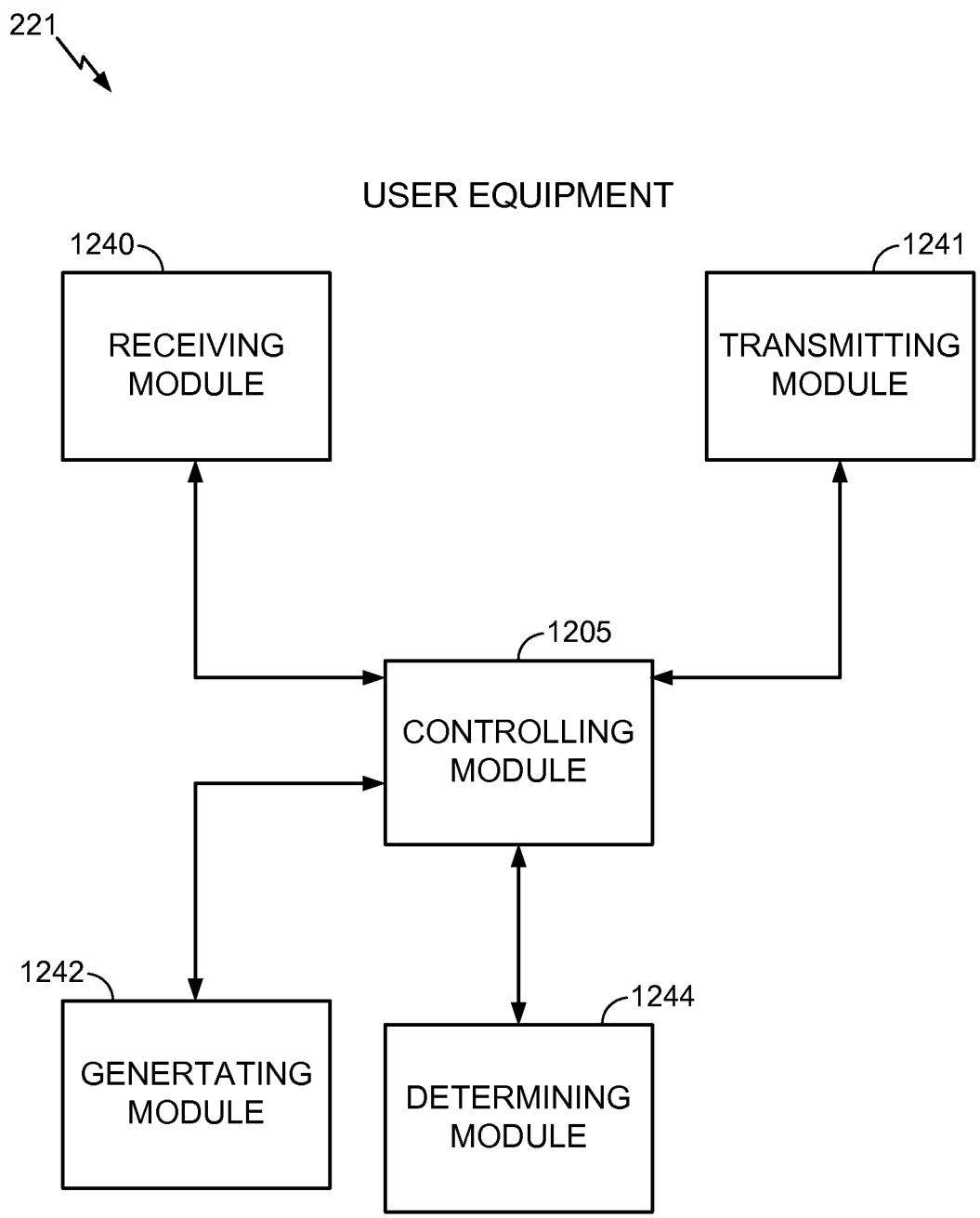
FIG. 12 is a functional block diagram of an exemplary user equipment in the communication network of FIG. 5.

FIG. 12 is a functional block diagram of an exemplary femto node in the communication network of FIG. 5. As shown, the UE 221 may comprise a controlling module 1205, a receiving module 1240, a transmitting module 1241, a generating module 1242, and a determining module 1244. The controlling module 1205 may correspond at least in some aspects to, for example, a processor or a processing module as discussed herein. The receiving module 1240 may correspond at least in some aspects to, for example, a receiver or a receiving module as discussed herein. The transmitting module 1241 may correspond at least in some aspects to, for example, a transmitter or a transmitting module as discussed herein. The generating module 1242 may correspond at least in some aspects to, for example, a processor or a processing module as discussed herein. The determining module 1244 may correspond at least in some aspects to, for example, a processor or a processing module as discussed herein.

Figure 13:
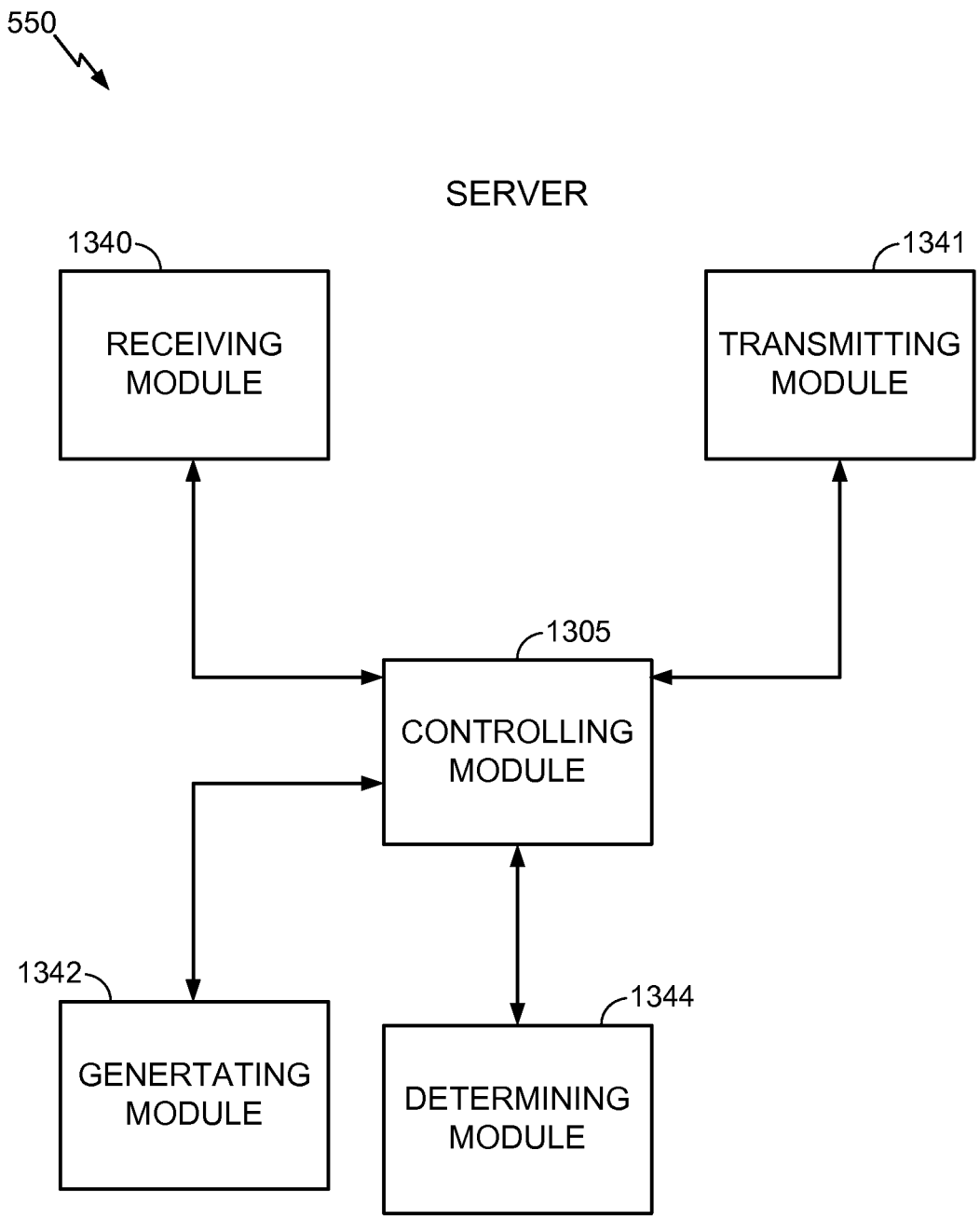
FIG. 13 is a functional block diagram of an exemplary user equipment in the communication network of FIG. 5.

FIG. 13 is a functional block diagram of an exemplary server 550 in the communication network of FIG. 5. As shown, the server 550 may comprise a controlling module 1305, a receiving module 1340, a transmitting module 1341, a generating module 1342, and a determining module 1344. The controlling module 1305 may correspond at least in some aspects to, for example, a processor or a processing module as discussed herein. The receiving module 1340 may correspond at least in some aspects to, for example, a receiver or a receiving module as discussed herein. The transmitting module 1341 may correspond at least in some aspects to, for example, a transmitter or a transmitting module as discussed herein. The generating module 1342 may correspond at least in some aspects to, for example, a processor or a processing module as discussed herein. The determining module 1244 may correspond at least in some aspects to, for example, a processor or a processing module as discussed herein.

The functionality of the modules of FIGS. 6-7B and 11-13 may be implemented in various ways consistent with the teachings herein. In some aspects the functionality of these modules may be implemented as one or more electrical components. In some aspects the functionality of these blocks may be implemented as a processing system including one or more processor components. In some aspects the functionality of these modules may be implemented using, for example, at least a portion of one or more integrated circuits (e.g., an ASIC). As discussed herein, an integrated circuit may include a processor, software, other related components, or some combination thereof. The functionality of these modules also may be implemented in some other manner as taught herein.

It should be understood that any reference to an element herein using a designation such as "first," "second," and so forth does not generally limit the quantity or order of those elements. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of: A, B, or C" used in the description or the claims means "A or B or C or any combination of these elements."

While the specification describes particular examples of the present invention, those of ordinary skill can devise variations of the present invention without departing from the inventive concept. For example, the teachings herein refer to circuit-switched network elements but are equally applicable to packet-switched domain network elements.

Those skilled in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those skilled in the art will further appreciate that the various illustrative logical blocks, modules, circuits, methods and algorithms described in connection with the examples disclosed herein may be implemented as electronic hardware, computer software, or combinations of both. To clearly illustrate this interchangeability of hardware and software, various illustrative components, blocks, modules, circuits, methods and algorithms have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the examples disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The methods or algorithms described in connection with the examples disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. A storage medium may be coupled to the processor such that the processor can read information from, and write information to, the storage medium. In the alternative, the storage medium may be integral to the processor. The processor and the storage medium may reside in an ASIC.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed examples is provided to enable any person skilled in the art to make or use the present invention. Various modifications to these examples will be readily apparent to those skilled in the art, and the generic principles defined herein may be applied to other examples without departing from the spirit or scope of the invention. Thus, the present invention is not intended to be limited to the examples shown herein but is to be accorded the widest scope consistent with the principles and novel features disclosed herein.

What is claimed is:

1. A method of communication, the method comprising:
   receiving, by a femto node, a first communication from a first apparatus, the first communication comprising an indication of offloading one or more processing tasks related to wireless communications to be performed at the first apparatus;
   performing, by the femto node, the one or more processing tasks offloaded from the first apparatus to the femto node; and
   selectively transmitting, by the femto node, a second communication to a second apparatus, the second communication comprising an indication of a result of the one or more processing tasks.

2. The method of claim 1, wherein the first communication is received by the femto node in response to a request sent from the femto node to the first apparatus.

3. The method of claim 1, wherein the first apparatus comprises a first user equipment.

4. The method of claim 3, wherein the one or more processing tasks comprise processing sensor data received from the first user equipment.

5. The method of claim 3, wherein the second apparatus comprises a server.

6. The method of claim 3, wherein the second apparatus comprises a second user equipment.

7. The method of claim 1, further comprising:
   receiving a third communication from a third apparatus comprising an indication of offloading one or more additional processing tasks related to wireless communications to be performed at the third apparatus; and
   performing the one or more additional processing tasks offloaded from the third apparatus to the femto node.

8. The method of claim 7, further comprising transmitting a fourth communication to a fourth apparatus, the fourth communication comprising an indication of a result of the one or more additional processing tasks.

9. The method of claim 1, wherein the first apparatus comprises a server.

10. The method of claim 9, wherein the second apparatus comprises a user equipment.

11. The method of claim 1, wherein the first communication further comprises data associated with the one or more processing tasks.

12. The method of claim 1, wherein the second communication further comprises data associated with the result of the one or more processing tasks.

13. The method of claim 1, further comprising waiting for a period of time between performing the one or more processing tasks and selectively transmitting the second communication.

14. The method of claim 1, further comprising:
   gathering information for performing the one or more processing tasks; and
   waiting for a period of time between gathering the information and performing the one or more processing tasks.

15. The method of claim 1, further comprising aggregating results for a plurality of the one or more processing tasks, wherein the indication of the result comprises the aggregated results.

16. The method of claim 1, wherein the indication comprises a request from the first apparatus to perform the one or more processing tasks.

17. The method of claim 1, wherein performing the one or more processing tasks comprises performing a portion of the one or more processing tasks, and wherein the method further comprises transferring a remaining portion of the one or more tasks back to the first apparatus.

18. The method of claim 1, wherein the one or more processing tasks comprise gathering information based on at least one user preference and transmitting at least a portion of the gathered information to the second apparatus.

19. The method of claim 18, wherein transmitting the second communication is performed at a future time relative to a time when the information is gathered.

20. The method of claim 19, wherein the future time is based on a prior configuration and/or handshaking between the femto node and the first and/or the second apparatus.

21. The method of claim 19, wherein the future time is based on a determination of a relevance of the gathered information, wherein the relevance is a function of a location and a time associated with the first apparatus and/or the second apparatus.

22. The method of claim 18, wherein the one or more processing tasks further comprise filtering the gathered information to generate the at least a portion of the gathered information based on the at least one user preference.

23. The method of claim 1, further comprising providing a database for storage and retrieval of information for the first apparatus.

24. The method of claim 23, further comprising enabling a remote retrieval of the information by the first apparatus, wherein the first apparatus is in communication with another node.

25. The method of claim 1, further comprising providing a plurality of silos for processing the one or more tasks, wherein each silo is associated with a different apparatus.

26. The method of claim 1, further comprising providing a plurality of silos for storage and retrieval of information, wherein each silo is associated with different apparatus.

27. The method of claim 1 wherein either the first apparatus or the second apparatus is a user equipment configured to enable a remote processing of tasks when not in a proximity of the femto node.

28. A femto node, comprising:
 a receiver configured to receive a first communication from a first apparatus, the first communication comprising an indication of offloading one or more processing tasks related to wireless communications to be performed at the first apparatus;
 a processor configured to perform the one or more processing tasks offloaded from the first apparatus to the femto node; and
 a transmitter configured to selectively transmit a second communication to a second apparatus, the second communication comprising an indication of a result of the one or more processing tasks.

29. The femto node of claim 28, wherein the transmitter is further configured to wait for a period of time after the one or more processing tasks are performed and before selectively transmitting the second communication.

30. The femto node of claim 28, wherein the processor is further configured to:
 gather information for performing the one or more processing tasks; and
 wait for a period of time between gathering the information and performing the one or more processing tasks.

31. The femto node of claim 28, wherein the processor is further configured to aggregate results for a plurality of the one or more processing tasks, and the indication of the result comprises the aggregated results.

32. The femto node of claim 28, wherein the one or more processing tasks comprise performing a portion of the one or more processing tasks, and the processor is configured to transfer a remaining portion of the one or more tasks back to the first apparatus.

33. The femto node of claim 28, wherein the one or more processing tasks comprise gathering information based on at least one user preference and transmitting at least a portion of the gathered information to the second apparatus.

34. The femto node of claim 33, wherein the transmitter is configured to transmit the second communication at a future time relative to a time when the information is gathered.

35. The femto node of claim 34, wherein the future time is based on a prior configuration and/or handshaking between the femto node and the first and/or the second apparatus.

36. The femto node of claim 34, wherein the future time is based on a determination of a relevance of the gathered information, wherein the relevance is a function of a location and a time associated with the first apparatus and/or the second apparatus.

37. The femto node of claim 33, wherein the one or more processing tasks further comprise filtering the gathered information to generate the at least a portion of the gathered information based on the at least one user preference.

38. The femto node of claim 28, further comprising a database for storage and retrieval of information for the first apparatus.

39. The femto node of claim 38, wherein the processor is further configured to enable a remote retrieval of the information by the first apparatus, and the first apparatus is in communication with another node.

40. The femto node of claim 28, wherein the processor is further configured to provide a plurality of silos for processing the one or more tasks, and each silo is associated with a different apparatus.

41. A femto node, comprising:
 means for receiving a first communication from a first apparatus, the first communication comprising an indication of offloading one or more processing tasks related to wireless communications to be performed at the first apparatus;
 means for performing the one or more processing tasks offloaded from the first apparatus to the femto node; and
 means for selectively transmitting a second communication to a second apparatus, the second communication comprising an indication of a result of the one or more processing tasks.

42. The femto node of claim 41, further comprising means for waiting for a period of time after the one or more processing tasks are performed and before the means for selectively transmitting the second communication.

43. The femto node of claim 41, wherein the means for performing the one or more processing tasks comprises means for performing a portion of the one or more processing tasks, and further comprising means for transferring a remaining portion of the one or more tasks back to the first apparatus.

44. The femto node of claim 41, wherein the one or more processing tasks comprise gathering information based on at least one user preference and transmitting at least a portion of the gathered information to the second apparatus.

45. The femto node of claim 44, wherein the one or more processing tasks further comprise filtering the gathered information to generate the at least a portion of the gathered information based on the at least one user preference.

46. A computer program product, comprising:
a non-transitory computer-readable medium, comprising:
- code for causing a computer of a femto node to receive a first communication from a first apparatus, the first communication comprising an indication of offloading one or more processing tasks related to wireless communications to be performed at the first apparatus;
- code for causing the computer to perform the one or more processing tasks offloaded from the first apparatus to the femto node; and
- code for causing the computer to selectively transmit a second communication to a second apparatus, the second communication comprising an indication of a result of the one or more processing tasks.

47. The computer program product of claim 46, wherein the computer-readable medium further comprises code for causing the computer to wait for a period of time between performing the one or more processing tasks and selectively transmitting the second communication.

48. The computer program product of claim 46, wherein the code for performing the one or more processing tasks comprises code for performing a portion of the one or more processing tasks, and wherein the computer-readable medium further comprises code for causing the computer to transfer a remaining portion of the one or more tasks back to the first apparatus.

* * * * *